US008183178B2

(12) United States Patent
Liu et al.

(10) Patent No.: US 8,183,178 B2
(45) Date of Patent: May 22, 2012

(54) ITERATED BRANCHING REACTION PATHWAYS VIA NUCLEIC ACID-MEDIATED CHEMISTRY

(75) Inventors: David R. Liu, Lexington, MA (US); Christopher T. Calderone, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 916 days.

(21) Appl. No.: 11/917,609

(22) PCT Filed: Jun. 16, 2006

(86) PCT No.: PCT/US2006/023654
§ 371 (c)(1),
(2), (4) Date: Aug. 18, 2008

(87) PCT Pub. No.: WO2006/138666
PCT Pub. Date: Dec. 28, 2006

(65) Prior Publication Data
US 2008/0318807 A1 Dec. 25, 2008

Related U.S. Application Data

(60) Provisional application No. 60/691,628, filed on Jun. 17, 2005.

(51) Int. Cl.
*C40B 40/00* (2006.01)
*C40B 50/00* (2006.01)
(52) U.S. Cl. .......................................... 506/16; 506/23
(58) Field of Classification Search ........................ None
See application file for complete search history.

(56) References Cited

U.S. PATENT DOCUMENTS

| | | | |
|---|---|---|---|
| 7,070,928 B2 | 7/2006 | Liu et al. |
| 7,223,545 B2 | 5/2007 | Liu et al. |
| 7,442,160 B2 | 10/2008 | Liu et al. |
| 7,491,494 B2 | 2/2009 | Liu et al. |
| 7,557,068 B2 | 7/2009 | Liu et al. |
| 7,771,935 B2 | 8/2010 | Liu et al. |
| 7,998,904 B2 | 8/2011 | Liu et al. |
| 8,017,323 B2 | 9/2011 | Liu et al. |
| 2003/0113738 A1 | 6/2003 | Liu et al. |
| 2004/0180412 A1 | 9/2004 | Liu et al. |
| 2008/0318807 A1 | 12/2008 | Liu et al. |
| 2009/0035824 A1 | 2/2009 | Liu et al. |
| 2009/0149347 A1 | 6/2009 | Liu et al. |
| 2009/0163371 A1 | 6/2009 | Stern et al. |
| 2009/0203530 A1 | 8/2009 | Liu et al. |
| 2010/0152099 A1 | 6/2010 | Lee et al. |
| 2011/0059458 A1 | 3/2011 | Huang et al. |
| 2011/0190141 A1 | 8/2011 | Liu et al. |

FOREIGN PATENT DOCUMENTS

| | | |
|---|---|---|
| WO | WO-00/23458 | 4/2000 |
| WO | WO-2004/024929 | 3/2004 |
| WO | WO-2004/039825 | 5/2004 |

OTHER PUBLICATIONS

Halpin et al. (PLoS Biology, 2004, 2(7):1022-1030).*
Gartner et al. (Science, 2004, 305(5690):1601).*
Li et al. (Agnew Chem Int Ed, 2004, 43:4848-4870).*
Bartel et al. (1993) "Isolation of new ribozymes from a large pool of random," *Science* 261:1411-1418.
Bunin et al. (1994) "The combinatorial synthesis and chemical and biological evaluation of a 1,4-benzodiazepine library," *Proc. Natl. Acad. Sci. USA* 91:4708-4712.
Burke et al. (2003) "Generating diverse skeletons of small molecules combinatorially," *Science* 302:613-618.
Burke et al. (2004) "A planning strategy for diversity-oriented synthesis," *Angew. Chem. Int. Ed.* 43:46-58.
Burke et al. (2004) "A synthesis strategy yielding skeletally diverse small molecules combinatorially," *J. Am. Chem. Soc.* 126:14095-14104.
Calderone et al. (2002) "Directing otherwise incompatible reactions in a single solution by using DNA-templated organic synthesis," *Angewandte Chemie Int. Ed.* 41(21):4104-4108.
Calderone et al. (2005) "Small-molecule diversification from iterated branching reaction pathways enabled by DNA-templated synthesis," *Angewandte Chemie Int. Ed.* 44:7383-7386.
Ding et al. (2002) "A combinatorial scaffold approach toward kinase-directed heterocycle libraries," *J. Am. Chem. Soc.* 124:1594-1596.
Doyon et al. (2003) "Highly sensitive in vitro selections for DNA-linked synthetic small molecules with protein binding affinity and specificity," *J. Am. Chem. Soc.* 125:12372-12373.
Examination Report of the European Patent Office for EP 06 785 057.8, dated Feb. 16, 2009, 3 pages.
Examination Report of the European Patent Office for EP 06 785 057.8, dated Jun. 2, 2008, 9 pages.
Früchtel et al. (1996) "Organic Chemistry on Solid Supports," *Angew. Chem. Int. Ed.* 35:17-42.
Furka et al. (1991) "General method for rapid synthesis of multicomponent peptide mixtures," *Int. J. Peptide Protein Res.* 37:487-493.
Gartner et al. (2002) "Expanding the reaction scope of DNA-templated synthesis," *Angew. Chem. Int. Ed.* 41:1796-1800.
Gartner et al. (2002) "Multistep small-molecule synthesis programmed by DNA templates," *J. Am. Chem. Soc.* 124:10304-10306.
Gartner et al. (2003) "Two Enabling Architectures for DNA-Templated Organic Synthesis," *Angew. Chem. Int. Ed.* 42:1370-1375.
Gartner et al. (2004) "DNA-templated organic synthesis and selection of a library of macrocycles," *Science* 305:1601-1605.
Halpin et al. (2004) "DNA display II. Genetic manipulation of combinatorial chemistry libraries for small-molecule evolution," *PLOS Biology* 2(7):1022-1030.
International Preliminary Report on Patentability for PCT/US2006/023654 dated Dec. 17, 2007, 11 pages.
International Search Report for PCT/US2006/023654 dated May 5, 2007, 8 pages.
Jaeger et al. (1999) "A complex ligase ribozyme evolved in vitro from a group I ribozyme domain," *Proc. Natl. Acad. Sci.* 96:14712-14717.
Jäschke et al. (2000) "Evolution of DNA and RNA as catalysts for chemical reactions " *Curr. Opin. Chem. Biol.* 4:257-262.

(Continued)

*Primary Examiner* — Stephanie K Mummert
(74) *Attorney, Agent, or Firm* — Goodwin Procter LLP

(57) ABSTRACT

The present invention provides methods and compositions for performing multi-step nucleic acid mediated synthesis of a highly diverse collection of molecules, for example, small molecules and polymers. In the method, in at least two steps, multiple reaction intermediates and/or products are produced in the same step by different chemical reactions.

18 Claims, 4 Drawing Sheets

OTHER PUBLICATIONS

Kanan et al. (2004) "Reaction discovery enabled by DNA-templated synthesis and in vitro selection," *Nature* 431:545-549.

Li et al. (2004) "Translation of DNA into Synthetic N-Acyloxazolidines," *J. Am. Chem. Soc.* 126:5090-5092.

Merrifield (1963) "Solid Phase Peptide Synthesis. I. The Synthesis of a Tetrapeptide," *J. Am. Chem. Soc.* 85:2149-2154.

Oguri et al. (2005) "Skeletal diversity via a folding pathway: synthesis of indole alkaloid-like skeletons," *Org. Lett.* 7:47-50.

Schreiber (1998) "Chemical Genetics Resulting from a Passion for Synthetic Organic Chemistry," *Bioorg. Med. Chem.* 6:1127-1152.

Sen et al. (1998) "DNA enzymes," *Curr. Opin. Chem Biol.* 2:680-687.

Stockwell (2004) "Exploring biology with small organic molecules," *Nature* 432:846-854.

Taylor et al. (2004) "Synthetic strategy toward skeletal diversity via solid-supported, otherwise unstable reactive intermediates," *Angew. Chem. Int. Ed.* 43:1681-1685.

* cited by examiner

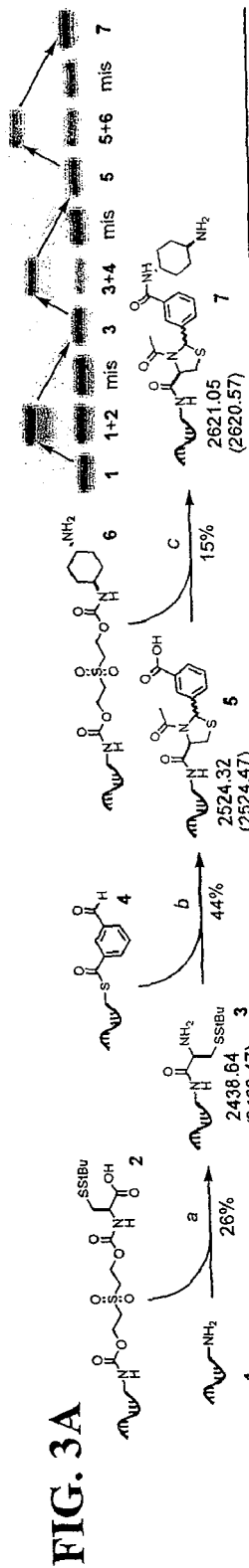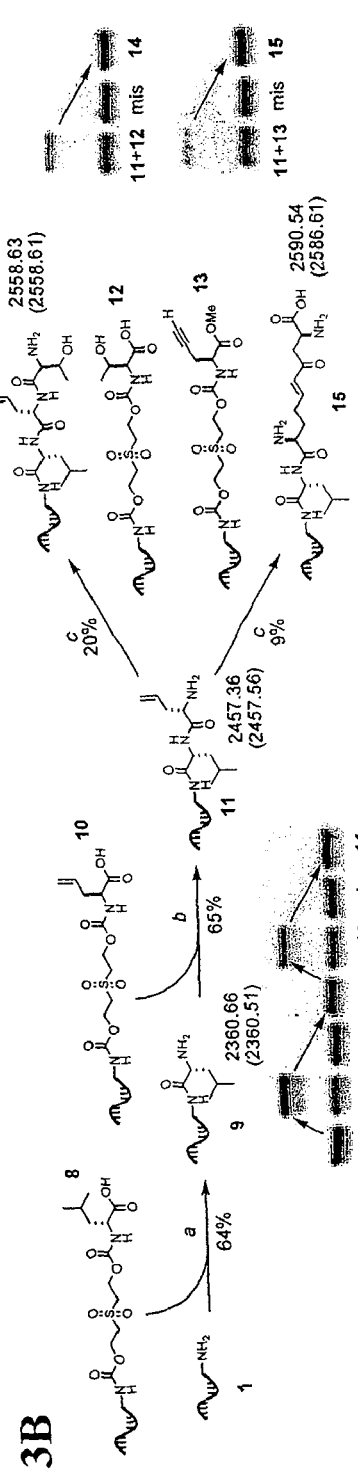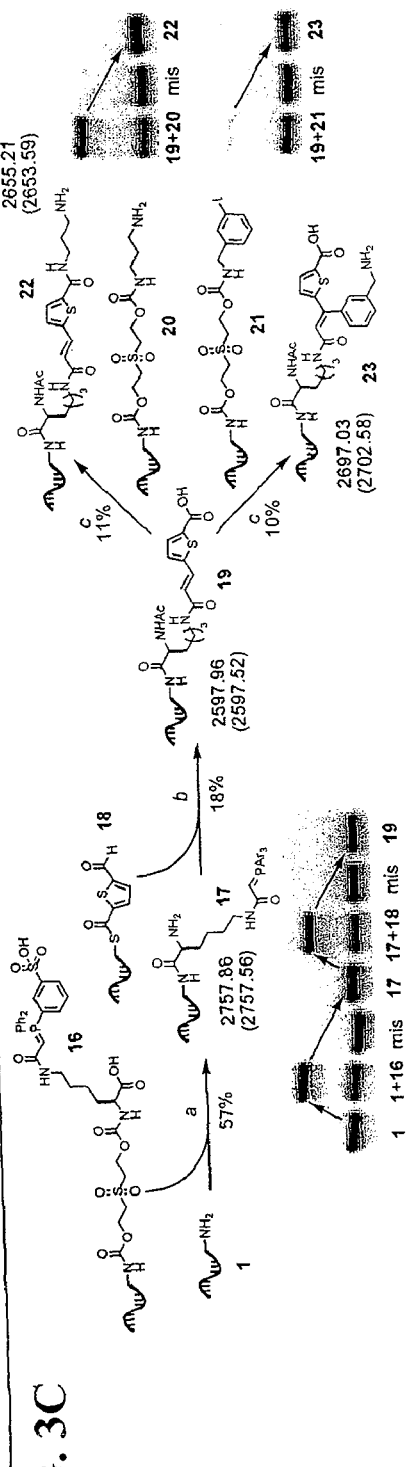
FIG. 3A
FIG. 3B
FIG. 3C

SEQUENCE LISTING

<160> NUMBER OF SEQ ID NOS: 54

<210> SEQ ID NO 1
<211> LENGTH: 50
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 1
ccatgcgaat tccataccag tcagcacact gtagcacgtt ctgagcctgc                50

<210> SEQ ID NO 2
<211> LENGTH: 52
<212> TYPE: DNA
<213> ORGANISM: Artificial Sequence
<220> FEATURE:
<223> OTHER INFORMATION: Synthesized oligonucleotide template sequence
      I

<400> SEQUENCE: 2
ccatgcgaat tctaggtagt actgtgcgat tgtgtcccta aagcttcctc ac             52

<210> SEQ ID NO 3
<211> LENGTH: 52
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 3
ccatgcgaat tcatacggta acactgcctt tctcccatca aagcttcctc ac             52

<210> SEQ ID NO 4
<211> LENGTH: 52
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 4
ccatgcgaat tctatccgat tgactgcctt tctcccatca aagcttcctc ac             52

<210> SEQ ID NO 5
<211> LENGTH: 52
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 5
ccatgcgaat tcttcttcct tcagcctagt agtccgtaga aagcttcctc ac             52

<210> SEQ ID NO 6
<211> LENGTH: 52

```
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 6
ccatgcgaat tcaacaacgt agagcctagt agtccgtaga aagcttcctc ac          52

<210> SEQ ID NO 7
<211> LENGTH: 15
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 7
agaacgtgct catgg                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 8
acagtgtgct catgg                                                    15

<210> SEQ ID NO 9
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 9
gactggtatg gacatgg                                                  17

<210> SEQ ID NO 10
<211> LENGTH: 15
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 10
agtacgtcct catgg                                                    15

<210> SEQ ID NO 11
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 11
gacacgaaag gacatgg                                                  17

<210> SEQ ID NO 12
<211> LENGTH: 15
<212> TYPE: DNA
<213> ORGANISM: Artificial Sequence
```

```
<220> FEATURE:
<223> OTHER INFORMATION: Synthesized oligonucleotide template, reagent
      or cassette sequence

<400> SEQUENCE: 12
tttagggaca aatgg                                                     15

<210> SEQ ID NO 13
<211> LENGTH: 15
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 13
tttgatggga aatgg                                                     15

<210> SEQ ID NO 14
<211> LENGTH: 15
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 14
tttctacgga aatgg                                                     15

<210> SEQ ID NO 15
<211> LENGTH: 16
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 15
caatcgcaca acatgg                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 16
gaaaggcagt acatgg                                                    16

<210> SEQ ID NO 17
<211> LENGTH: 16
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 17
ctactaggct acatgg                                                    16

<210> SEQ ID NO 18
<211> LENGTH: 17
<212> TYPE: DNA
<213> ORGANISM: Artificial Sequence
<220> FEATURE:
<223> OTHER INFORMATION: Synthesized oligonucleotide template, reagent
``` or cassette sequence

<400> SEQUENCE: 18
gtactaccta gacatgg                                                17

<210> SEQ ID NO 19
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 19
gttaccgtat gacatgg                                                17

<210> SEQ ID NO 20
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 20
caatcggata gacatgg                                                17

<210> SEQ ID NO 21
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 21
gaaggaacaa gacatgg                                                17

<210> SEQ ID NO 22
<211> LENGTH: 17
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 22
ctacgttgtt gacatgg                                                17

<210> SEQ ID NO 23
<211> LENGTH: 20
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 23
ccatgcgaat tctaggtagt                                             20

<210> SEQ ID NO 24
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

```
<400> SEQUENCE: 24
cagtactacc ta                                                         12

<210> SEQ ID NO 25
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 25
actgtgcgat                                                            10

<210> SEQ ID NO 26
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 26
cacaatcgca                                                            10

<210> SEQ ID NO 27
<211> LENGTH: 22
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 27
tgtgtcccta aagcttcctc ac                                              22

<210> SEQ ID NO 28
<211> LENGTH: 8
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 28 tttaggga                                                               8

<210> SEQ ID NO 29
<211> LENGTH: 20
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 29
ccatgcgaat tcatacggta                                                 20

<210> SEQ ID NO 30
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 30
```
gtgttaccgt at                                                                   12

<210> SEQ ID NO 31
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 31
acactgcctt                                                                      10

<210> SEQ ID NO 32
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 32
gagaaaggca                                                                      10

<210> SEQ ID NO 33
<211> LENGTH: 22
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 33
tctcccatca aagcttcctc ac                                                        22

<210> SEQ ID NO 34
<211> LENGTH: 8
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 34 tttgatgg                                                                         8

<210> SEQ ID NO 35
<211> LENGTH: 20
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 35
ccatgcgaat tctatccgat                                                           20

<210> SEQ ID NO 36
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 36
gtcaatcgga ta                                                                   12

<210> SEQ ID NO 37
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 37
tgactgcctt                                                          10

<210> SEQ ID NO 38
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 38
gagaaaggca                                                          10

<210> SEQ ID NO 39
<211> LENGTH: 22
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 39
tctcccatca aagcttcctc ac                                            22

<210> SEQ ID NO 40
<211> LENGTH: 8
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 40 tttgatgg                                                             8

<210> SEQ ID NO 41
<211> LENGTH: 20
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 41
ccatgcgaat tcttgttcct                                               20

<210> SEQ ID NO 42
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 42
ctgaaggaac aa                                                       12

<210> SEQ ID NO 43

```
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 43
tcagcctagt                                                               10

<210> SEQ ID NO 44
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 44
gactgctagg                                                               10

<210> SEQ ID NO 45
<211> LENGTH: 22
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 45
agtccgtaga aagcttcctc ac                                                 22

<210> SEQ ID NO 46
<211> LENGTH: 8
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 46 tttctacg                                                                  8

<210> SEQ ID NO 47
<211> LENGTH: 20
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 47
ccatgcgaat tcaacaacgt                                                    20

<210> SEQ ID NO 48
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 48
ctctacgttg tt                                                            12

<210> SEQ ID NO 49
<211> LENGTH: 10
<212> TYPE: DNA
```

```
<213> ORGANISM: Artificial Sequence
<220> FEATURE:
<223> OTHER INFORMATION: Synthesized oligonucleotide template, reagent
      or cassette sequence

<400> SEQUENCE: 49
agagcctagt                                                                10

<210> SEQ ID NO 50
<211> LENGTH: 10
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 50
gactactagg                                                                10

<210> SEQ ID NO 51
<211> LENGTH: 22
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 51
agtccgtaga aagcttcctc ac                                                  22

<210> SEQ ID NO 52
<211> LENGTH: 8
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 52 tttctacg                                                                   8

<210> SEQ ID NO 53
<211> LENGTH: 18
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 53
ggtatggaat tcgcatgg                                                       18

<210> SEQ ID NO 54
<211> LENGTH: 12
<212> TYPE: DNA
<213> ORGANISM: Artificial Sequence
<220> FEATURE:
<223> OTHER INFORMATION: Synthesized oligonucleotide template, reagent
      or cassette sequence

<400> SEQUENCE: 54
gaattcgcat gg                                                             12
```

ITERATED BRANCHING REACTION PATHWAYS VIA NUCLEIC ACID-MEDIATED CHEMISTRY

RELATED APPLICATIONS

This application is the national stage of International (PCT) Patent Application Serial No. PCT/US2006/023654, filed Jun. 16, 2006, and published under PCT Article 21(2) in English, which claims the benefit of and priority to U.S. Patent Application Ser. No. 60/691,628, filed Jun. 17, 2005, the entire disclosure of each of which is incorporated by reference herein for all purposes.

GOVERNMENT FUNDING

This invention was made with Government support under the Office of Naval Research awards N00014-03-1-0749, N00014-00-1-0596, and National Institutes of Health award GM65865. The Government has certain rights in the invention.

FIELD OF THE INVENTION

The invention relates generally to nucleic acid-mediated chemistry. More particularly, the invention relates to iterated branching reaction pathways mediated by nucleic acid-mediated chemistry.

BACKGROUND OF THE INVENTION

As synthetic small molecules continue to interface with an increasingly large swath of biology (Stockwell (2004) NATURE 432: 846; Schreiber (1996) BIOORG. MED. CHEM. 6: 1127), researchers have sought new approaches to rapidly create highly diverse collections of small molecules (Burke et al. (2004) ANGEW. CHEM., INT. ED. 43: 46). Early small-molecule libraries generally contained a single core scaffold decorated by different chemical groups (Bunin et al. (1994) PROC. NATL. ACAD. SCI. U.S.A. 91: 4708). Later efforts introduced modest structural variation in the central scaffold (Ding et al. (2002) J. AM. CHEM. SOC. 124: 1594).

The vast majority of current library synthesis efforts are based on solid-phase, split-pool methodologies (Furka et al. (1991) INT. J. PEPT. PROTEIN RES. 37: 487; Merrifield (1963) J. AM. CHEM. SOC. 85: 2149). While these methods offer technical advantages, they also limit the diversity of structures that can be created. Notably, it is generally not possible to direct a specific fraction of beads (for example, those beads containing molecules with a primary amine group) to one of several possible subsequent reaction conditions (for example, exposure to an acylating agent). As a result, every intermediate in a split-pool library synthesis must be reactive toward any reactant it may encounter in a subsequent step. Moreover, it usually is not possible to purify unreacted support-bound starting material away from desired products after each library synthesis step, so only highly efficient reactions can be used. These limitations constrain the amount of diversity that can be borne in early steps of a library synthesis. As a result, the diversification of scaffolds during library synthesis has thus far been limited to a single (predominantly terminal) step (Burke et al. (2003), SCIENCE 302, 613; Burke et al. (2004) J. AM. CHEM. SOC. 126: 14095; Oguri et al. (2005) ORG. LETT. 7: 47; Taylor et al. (2004) ANGEW. CHEM., INT. ED. 43: 1681).

Thus, there remains a need for efficient and effective methodologies that permit iterative branching reaction pathways to occur in a single reaction mixture at each step in a synthetic scheme for producing a library of compounds.

SUMMARY

The present invention is based, in part, upon the discovery that during the synthesis of compound libraries requiring multiple reaction steps, it is possible to perform multiple branching reaction pathways at each step, wherein each of the pathways can create different products. As a result, it is possible to simultaneously generate different products by different reaction pathways at each step during a multi-step synthesis scheme. These new approaches provide a broader spectrum of multi-step products, such as synthetic small molecules and synthetic polymers, than can be created during library synthesis.

In one aspect, the invention provides a multi-step in vitro method for producing multiple reaction products in a single reaction mixture. The method comprises combining in a reaction vessel (i) a plurality of different templates, wherein each template comprises a reactive unit associated with an oligonucleotide sequence comprising a plurality of codons, and (ii) a plurality of different transfer units, wherein each transfer unit comprises a reactive unit associated with an oligonucleotide sequence comprising an anti-codon capable of annealing to a codon present in at least one of the templates. The templates and transfer units are combined together under conditions to permit a plurality of different transfer units to anneal to a corresponding plurality of templates so that the reactive units of each template react with the reactive unit of each transfer unit to produce a plurality of different reaction intermediates, wherein each different reaction intermediate is associated with the template that encoded its synthesis. Then, the different reaction intermediates are combined in the same reaction vessel or in a different reaction vessel with a plurality of transfer units, wherein each transfer unit comprises a reactive unit associated with an oligonucleotide sequence comprising an anti-codon capable of annealing to a codon present in at least one of the templates. The reaction intermediates and templates are combined under conditions to permit a plurality of the transfer units to anneal to a corresponding plurality of templates so that the reactive unit of a transfer unit reacts with at least one reaction intermediate to produce a reaction product, wherein each reaction product is associated with the template that encoded its synthesis.

The method optionally further includes the additional step of, after the first combining step but before the second combining step, harvesting or collecting the reaction intermediates. The method optionally further includes the additional step of, after producing the reaction products, selecting a reaction product associated with a template oligonucleotide that encoded its synthesis.

In the first combining step, at least two, or at least three of the reaction intermediates are produced by different chemical reactions, i.e., different chemical pathways. In addition or in the alternative, in the second combining step, at least two, or at least three reaction products are produced by different chemical reactions.

In another aspect, the invention provides a multi-step in vitro method for producing multiple reaction products in a single reaction mixture. The method comprises combining in a single solution (i) a first template comprising a first reactive unit associated with an oligonucleotide sequence comprising first codon and a second codon, (ii) a second template comprising a first reactive unit associated with an oligonucleotide sequence comprising first codon and a second codon, wherein the second codons of the first and second templates have different oligonucleotide sequences, (iii) a third template comprising a second reactive unit associated with an oligonucleotide sequence comprising a first codon and a second codon, wherein the first and second codons of the third template have different oligonucleotide sequences from the first and second codons of both the first and second templates, (iv) at least two first transfer units each comprising a first reactive unit associated with an oligonucleotide sequence comprising an anti-codon capable of annealing to a codon sequence present in both the first and second templates, and (v) a second transfer unit comprising a second reactive unit associated with an oligonucleotide sequence comprising an anti-codon capable of annealing to a codon sequence present in the third template.

The templates and transfer units are combined under conditions to permit (i) a first transfer unit to anneal to the first template so that the first reactive unit of the template reacts with the first reactive unit of the transfer unit to produce a first reaction intermediate associated with the first template, (ii) another first transfer unit to anneal to the second template so that the first reactive unit of the second template reacts with the first reactive unit of the transfer unit to produce a second reaction intermediate associated with the second template, and (iii) the second transfer unit to anneal to the third template so that the second reactive unit of the second transfer unit reacts with the second reactive unit of the third template to produce a third reaction intermediate associated with the third template.

The first reaction intermediate, the second reaction intermediate, and third reaction intermediate then are collected and are then combined in a single solution with (i) a third transfer unit comprising a third reactive unit associated with an oligonucleotide sequence comprising an anti-codon capable of annealing to a codon sequence present in the first template, (ii) a fourth transfer unit comprising a fourth reactive unit associated with an oligonucleotide sequence comprising an anti-codon capable of annealing to a codon sequence present in the second template, and (iii) a fifth transfer unit comprising a fifth reactive unit associated with an oligonucleotide sequence comprising an anti-codon capable of annealing to a codon sequence present in the third template. The reaction intermediates and transfer units are combined under conditions to permit (i) the third transfer unit to anneal to the first template so that the third reactive unit of the third transfer unit reacts with the first reaction intermediate to produce a first product, (ii) the fourth transfer unit to anneal to the second template so that the fourth reactive unit of the fourth transfer unit reacts with the second reaction intermediate to produce a second product, and (iii) the fifth transfer unit to anneal to the third template so that the fifth reactive unit of the fifth transfer unit reacts with the third reaction intermediate to produce a third product.

The method also comprises the optional additional step of after producing the reaction products, selecting a reaction product associated with a template oligonucleotide that encoded its synthesis. In the method, the second and third reaction intermediates can be produced by different chemical reactions (i.e., different reaction pathways). In addition, the first, second and, third reaction intermediates can be produced by different chemical reactions. In addition, the second and third reaction products can be produced by different chemical reactions. Furthermore, the first, second and third reaction products can be produced by different chemical reactions.

In another aspect, the invention provides a multi-step in vitro method for producing multiple reaction products in a single reaction mixture. The method comprises combining in a single solution (i) a first template comprising a first reactive unit associated with an oligonucleotide sequence comprising first codon and a second codon, (ii) a second template comprising a first reactive unit associated with an oligonucleotide sequence comprising first codon and a second codon, wherein the second codons of the first and second templates have different oligonucleotide sequences, (iii) a third template comprising a second reactive unit associated with an oligonucleotide sequence comprising first codon and a second codon, wherein the first and second codons of the third template have different oligonucleotide sequences from the first and second codons of both the first and second templates, (iv) a first transfer unit each comprising a first reactive unit associated with an oligonucleotide sequence comprising an anti-codon capable of annealing to a codon sequence present in the first template, (v) a second transfer unit each comprising a second reactive unit associated with an oligonucleotide sequence comprising an anti-codon capable of annealing to a codon sequence present in the second template, and (vi) a third transfer unit comprising a third reactive unit associated with an oligonucleotide sequence comprising an anti-codon capable of annealing to a codon sequence present in the third template.

The templates and transfer units are combined under conditions to permit (i) the first transfer unit to anneal to the first template so that the first reactive unit of the first template reacts with the first reactive unit of the transfer unit to produce a first reaction intermediate associated with the first template, (ii) the second transfer unit to anneal to the second template so that the second reactive unit of the second template reacts with the second reactive unit of the transfer unit to produce a second reaction intermediate associated with the second template, and (iii) the third transfer unit to anneal to the third template so that the third reactive unit of the third transfer unit reacts with the third reactive unit of the third template to produce a third reaction intermediate associated with the third template.

The first reaction intermediate, the second reaction intermediate, and third reaction intermediate are then collected and are then combined in a single solution with (i) a fourth transfer unit comprising a fourth reactive unit associated with an oligonucleotide sequence comprising an anti-codon capable of annealing to a codon sequence present in the first template, and (ii) a fifth transfer unit comprising a fifth reactive unit associated with an oligonucleotide sequence comprising an anti-codon capable of annealing to a codon sequence present in the third template. The reaction intermediates and transfer units are combined under conditions to permit (i) the fourth transfer unit to anneal to the first template so that the fourth reactive unit of the fourth transfer unit reacts with the first reaction intermediate to produce a first product, and (ii) the fifth transfer unit to anneal to the third template so that the fifth reactive unit of the fifth transfer unit reacts with the third reaction intermediate to produce a third product.

In this method, the reaction intermediates and transfer units optionally are combined in a solution so that a sixth transfer unit comprising a sixth reactive unit associated with an oligonucleotide sequence comprising an anti-codon capable of annealing to a codon sequence present in the second template and the sixth transfer unit anneals to the second template so that the sixth reactive unit of the sixth transfer unit reacts with the second reaction intermediate to produce a second product. The method also comprises the optional additional step of after producing the reaction products, selecting a reaction product associated with a template oligonucleotide that encoded its synthesis. In this method, the first and second reaction intermediates can be produced by different chemical reactions. In addition, the first, second and third reaction intermediates can be produced by different chemical reactions. In addition, the first and third products can be produced by different chemical reactions. In addition, the first, second and third products can be produced by different chemical reactions.

In another aspect, the invention provides an improved method of performing a multi-step nucleic acid-mediated synthetic scheme using templates containing reactive units and transfer units containing reactive units. The improvement comprises: (a) in a first solution, performing at least two different nucleic acid-mediated chemical reactions to produce at least two different reaction intermediates from templates associated with reactive units having the same chemical functionality; and (b) in a second, different solution, performing at least two different nucleic acid-mediated chemical reactions to produce at least two different reaction products from the at least two reaction intermediates, wherein the reaction products are associated with the templates that encoded their synthesis.

In this approach, the reactive units can be covalently attached to the templates. In addition or in the alternative, the reaction intermediates can be covalently attached to the templates that encoded their synthesis. In addition or in the alternative, the reaction products are covalently attached to the templates that encoded their synthesis.

In addition, the invention provides a library of chemical compounds prepared by any of the foregoing methods.

The foregoing aspects and embodiments of the invention may be more fully understood by reference to the following definitions, figures, detailed description and claims.

DEFINITIONS

The term, "associated with" as used herein describes the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be, for example, but without limitation, through an amide, ester, carbon-carbon, disulfide, carbamate, ether, thioether, urea, amine, or carbonate linkage. The covalent association may also include a linker moiety, for example, a photocleavable linker. Desirable non-covalent interactions include hydrogen bonding, van der Waals interactions, dipole-dipole interactions, pi stacking interactions, hydrophobic interactions, magnetic interactions, electrostatic interactions, etc. Also, two or more entities or agents may be "associated with" one another by being present together in the same composition.

The term, "biological macromolecule" as used herein refers to a polynucleotide (e.g., RNA, DNA, RNA/DNA hybrid), protein, peptide, lipid, or polysaccharide. The biological macromolecule may be naturally occurring or non-naturally occurring. In a preferred embodiment, a biological macromolecule has a molecular weight greater than about 5,000 Daltons.

The terms, "polynucleotide," "nucleic acid", or "oligonucleotide" as used herein refer to a polymer of nucleotides, at least three nucleotides in length. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), a threose nucleic acid (TNA) and any other polymers capable of serving as a template for an amplification reaction using an amplification technique, for example, a polymerase chain reaction, a ligase chain reaction, or non-enzymatic template-directed replication.

The term, "small molecule" as used herein, refers to an organic compound either synthesized in the laboratory or found in nature having a molecular weight less than 10,000 grams per mole, optionally less than 5,000 grams per mole, and optionally less than 2,000 grams per mole.

The terms, "small molecule scaffold" or "molecular scaffold" as used herein, refer to a chemical compound having at least one site or chemical moiety suitable for functionalization. The small molecule scaffold or molecular scaffold may have two, three, four, five or more sites or chemical moieties suitable for functionalization. These functionalization sites may be protected or masked as would be appreciated by one of skill in this art. The sites may also be found on an underlying ring structure or backbone.

The term, "transfer unit" as used herein, refers to a molecule comprising an oligonucleotide having an anti-codon sequence associated with a reactive unit including, for example, but not limited to, a building block, monomer, monomer unit, molecular scaffold, or other reactant useful in template mediated chemical synthesis.

The term, "template" as used herein, refers to a molecule comprising an oligonucleotide having at least one codon sequence suitable for a template mediated chemical synthesis. The template optionally may comprise (i) a plurality of codon sequences, (ii) an amplification means, for example, a PCR primer binding site or a sequence complementary thereto, (iii) a reactive unit associated therewith, (iv) a combination of (i) and (ii), (v) a combination of (i) and (iii), (vi) a combination of (ii) and (iii), or a combination of (i), (ii) and (iii).

The terms, "codon" and "anti-codon" as used herein, refer to complementary oligonucleotide sequences in the template and in the transfer unit, respectively, that permit the transfer unit to anneal to the template during template mediated chemical synthesis.

BRIEF DESCRIPTION OF THE DRAWINGS

The invention may be further understood from the following figures in which:

FIG. 3A-3C demonstrate individual validation of five reaction pathways. Template amine 1 was separately treated with complementary oligonucleotide 2 (FIG. 3A), complementary oligonucleotide 8 (FIG. 3B), or complementary oligonucleotide 16 (FIG. 3C), to yield final products 7 (FIG. 3A), 14 and 15 (FIG. 3B), or 22 and 23 (FIG. 3C). In each denaturing polyacrylamide gel electrophoresis (PAGE) image, lower bands represent template 1 or functionalized derivatives thereof, and upper bands represent covalently linked template-reagent pairs. Each cleaved intermediate was digested with EcoRI and subjected to mass-spectrometric analysis, with observed and (expected) masses given. To verify reaction sequence specificity of each DNA-templated reaction, a sample of each template intermediate was treated with a reagent oligonucleotide containing a scrambled DNA sequence ("mis"). Reaction (a) conditions included 20 mM EDC, 15 mM s-NHS, pH 6.0, 12 hours, 23° C., then pH 10.0 buffer, 2 hours, 37° C. Reaction (b) conditions included 25 mM 1,4-dithiothreitol (DTT), pH 8.5, 1 hour, 37° C., then pH 7.0 buffer, 90 minutes, then 20 mM EDC, 15 mM s-NHS, 12 hours, 23° C., then $\frac{1}{200}$ volume $Ac_2O$, 1 hour, then pH 12.0 buffer, 10 mM 2-mercaptoethanol, 1 hour, 37° C. Reaction (c) conditions included 1 M NaBr, 50 µM $Na_2PdCl_4$, pH 6.0, 4 hours, 37° C., then 25 mM DTT, 10 minutes, 85° C., then 20 mM EDC, 15 mM s-NHS, pH 6.0, 12 hours, 23° C., then pH 12.0 buffer, 30 minutes, 23° C.

DESCRIPTION OF THE INVENTION

Figure 1:
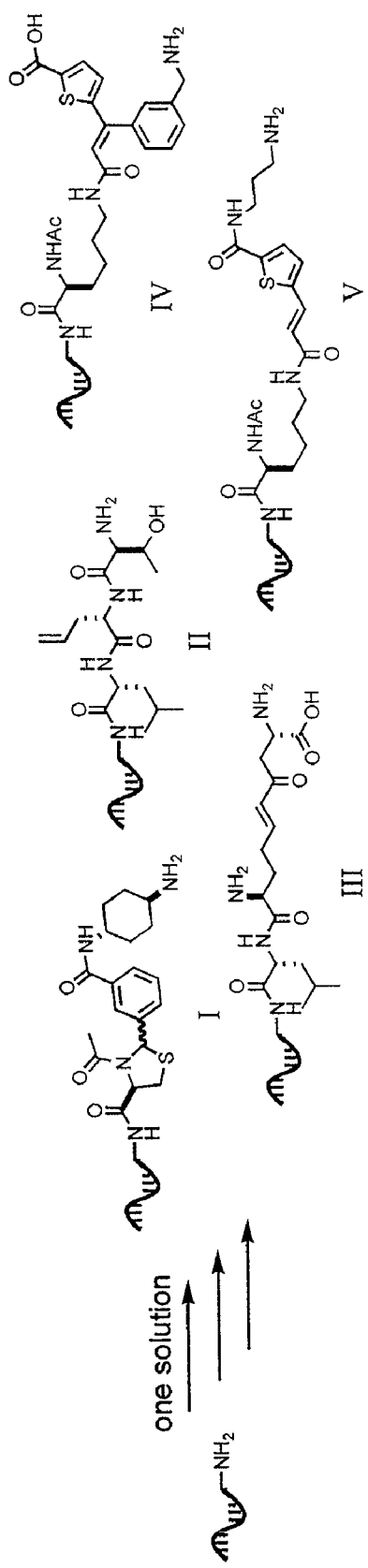
FIG. 1 is a schematic representation of exemplary compounds that can be produced simultaneously in a single reaction mixture from templates containing a primary amine.

The present invention is based, in part, upon discovery that it is possible to generate a library of different compounds by a multi-step reaction scheme, where in each of the steps it is possible to simultaneously generate multiple reaction intermediates and/or reaction products by different reaction pathways. For example, at each step, it is possible to generate multiple products from the same or similar starting materials by virtue of the fact that multiple different chemical reactions can occur simultaneously on the starting materials to produce different reaction products.

In one aspect, the invention provides a multi-step in vitro method for producing multiple reaction products in a single reaction mixture. The method comprises combining in a reaction vessel (i) a plurality of different templates, wherein each template comprises a reactive unit associated with an oligonucleotide sequence comprising a plurality of codons, and (ii) a plurality of different transfer units, wherein each transfer unit comprises a reactive unit associated with an oligonucleotide sequence comprising an anti-codon capable of annealing to a codon present in at least one of the templates. The templates and transfer units are combined together under conditions to permit a plurality of transfer units to anneal to a corresponding plurality of templates so that the reactive units of each template react with the reactive unit of each transfer unit to produce a plurality of different reaction intermediates, wherein each different reaction intermediate is associated with the template that encoded its synthesis. The different reaction intermediates then are combined in the same reaction vessel or in a different reaction vessel with a plurality of transfer units, wherein each transfer unit comprises a reactive unit associated with an oligonucleotide sequence comprising an anti-codon capable of annealing to a codon present in at least one of the templates. The reaction intermediates and templates are combined under conditions to permit a plurality of the transfer units to anneal to a corresponding plurality of templates so that the reactive unit of a transfer unit reacts with at least one reaction intermediate to produce a reaction product, wherein each reaction product is associated with the template that encoded its synthesis.

The method optionally further includes the additional step of, after the first combining step but before the second combining step harvesting or collecting the reaction intermediates. The method optionally further includes the additional step of, after producing the reaction products, selecting a reaction product associated with a template oligonucleotide that encoded its synthesis.

In the first combining step, at least two, or at least three of the reaction intermediates are produced by different chemical reactions, i.e., different chemical pathways. In addition or in the alternative, in the second combining step, at least two, or at least three reaction products are produced by different chemical reactions.

In another aspect, the invention provides a multi-step in vitro method for producing multiple reaction products in a single reaction mixture. The method comprises combining in a single solution (i) a first template comprising a first reactive unit associated with an oligonucleotide sequence comprising first codon and a second codon, (ii) a second template comprising a first reactive unit associated with an oligonucleotide sequence comprising first codon and a second codon, wherein the second codons of the first and second templates have different oligonucleotide sequences, (iii) a third template comprising a second reactive unit associated with an oligonucleotide sequence comprising a first codon and a second codon, wherein the first and second codons of the third template have different oligonucleotide sequences from the first and second codons of both the first and second templates, (iv) at least two first transfer units each comprising a first reactive unit associated with an oligonucleotide sequence comprising an anti-codon capable of annealing to a codon sequence present in both the first and second templates, and (v) a second transfer unit comprising a second reactive unit associated with an oligonucleotide sequence comprising an anti-codon capable of annealing to a codon sequence present in the third template.

The templates and transfer units are combined under conditions to permit (i) a first transfer unit to anneal to the first template so that the first reactive unit of the template reacts with the first reactive unit of the transfer unit to produce a first reaction intermediate associated with the first template, (ii) another first transfer unit to anneal to the second template so that the first reactive unit of the second template reacts with the first reactive unit of the transfer unit to produce a second reaction intermediate associated with the second template, and (iii) the second transfer unit to anneal to the third template so that the second reactive unit of the second transfer unit reacts with the second reactive unit of the third template to produce a third reaction intermediate associated with the third template.

The first reaction intermediate, the second reaction intermediate, and third reaction intermediate then are collected and are then combined in a single solution with (i) a third transfer unit comprising a third reactive unit associated with an oligonucleotide sequence comprising an anti-codon capable of annealing to a codon sequence present in the first template, (ii) a fourth transfer unit comprising a fourth reactive unit associated with an oligonucleotide sequence comprising an anti-codon capable of annealing to a codon sequence present in the second template, and (iii) a fifth transfer unit comprising a fifth reactive unit associated with an oligonucleotide sequence comprising an anti-codon capable of annealing to a codon sequence present in the third template. The reaction intermediates and transfer units are combined under conditions to permit (i) the third transfer unit to anneal to the first template so that the third reactive unit of the third transfer unit reacts with the first reaction intermediate to produce a first product, (ii) the fourth transfer unit to anneal to the second template so that the fourth reactive unit of the fourth transfer unit reacts with the second reaction intermediate to produce a second product, and (iii) the fifth transfer unit to anneal to the third template so that the fifth reactive unit of the fifth transfer unit reacts with the third reaction intermediate to produce a third product.

The method also comprises the optional additional step of after producing the reaction products, selecting a reaction product associated with a template oligonucleotide that encoded its synthesis. In the method, the second and third reaction intermediates can be produced by different chemical reactions (i.e., different reaction pathways). In addition, the first, second, and third reaction intermediates can be produced by different chemical reactions. In addition, the second and third reaction products can be produced by different chemical reactions. Furthermore, the first, second, and third reaction products can be produced by different chemical reactions.

In another aspect, the invention provides a multi-step in vitro method for producing multiple reaction products in a single reaction mixture. The method comprises combining in a single solution (i) a first template comprising a first reactive unit associated with an oligonucleotide sequence comprising first codon and a second codon, (ii) a second template comprising a first reactive unit associated with an oligonucleotide sequence comprising first codon and a second codon, wherein the second codons of the first and second templates have different oligonucleotide sequences, (iii) a third template comprising a second reactive unit associated with an oligonucleotide sequence comprising first codon and a second codon, wherein the first and second codons of the third template have different oligonucleotide sequences from the first and second codons of both the first and second templates, (iv) a first transfer unit each comprising a first reactive unit associated with an oligonucleotide sequence comprising an anti-codon capable of annealing to a codon sequence present in the first template, (v) a second transfer unit each comprising a second reactive unit associated with an oligonucleotide sequence comprising an anti-codon capable of annealing to a codon sequence present in the second template, and (vi) a third transfer unit comprising a third reactive unit associated with an oligonucleotide sequence comprising an anti-codon capable of annealing to a codon sequence present in the third template.

The templates and transfer units are combined under conditions to permit (i) the first transfer unit to anneal to the first template so that the first reactive unit of the first template reacts with the first reactive unit of the transfer unit to produce a first reaction intermediate associated with the first template, (ii) the second transfer unit to anneal to the second template so that the second reactive unit of the second template reacts with the second reactive unit of the transfer unit to produce a second reaction intermediate associated with the second template, and (iii) the third transfer unit to anneal to the third template so that the third reactive unit of the third transfer unit reacts with the third reactive unit of the third template to produce a third reaction intermediate associated with the third template.

The first reaction intermediate, the second reaction intermediate, and third reaction intermediate are then collected and are then combined in a single solution with (i) a fourth transfer unit comprising a fourth reactive unit associated with an oligonucleotide sequence comprising an anti-codon capable of annealing to a codon sequence present in the first template, and (ii) a fifth transfer unit comprising a fifth reactive unit associated with an oligonucleotide sequence comprising an anti-codon capable of annealing to a codon sequence present in the third template. The reaction intermediates and transfer units are combined under conditions to permit (i) the fourth transfer unit to anneal to the first template so that the fourth reactive unit of the fourth transfer unit reacts with the first reaction intermediate to produce a first product, and (ii) the fifth transfer unit to anneal to the third template so that the fifth reactive unit of the fifth transfer unit reacts with the third reaction intermediate to produce a third product.

In this method, the reaction intermediates and transfer units optionally are combined in a solution so that a sixth transfer unit comprising a sixth reactive unit associated with an oligonucleotide sequence comprising an anti-codon capable of annealing to a codon sequence present in the second template and the sixth transfer unit anneals to the second template so that the sixth reactive unit of the sixth transfer unit reacts with the second reaction intermediate to produce a second product. The method also comprises the optional additional step of after producing the reaction products, selecting a reaction product associated with a template oligonucleotide that encoded its synthesis. In this method, the first and second reaction intermediates can be produced by different chemical reactions. In addition, the first, second and third reaction intermediates can be produced by different chemical reactions. In addition, the first and third products can be produced by different chemical reactions. In addition, the first, second and third products can be produced by different chemical reactions.

In another aspect, the invention provides an improved method of performing a multi-step nucleic acid-mediated synthetic scheme using templates containing reactive units and transfer units containing reactive units. The improvement comprises: (a) in a first solution, performing at least two different nucleic acid-mediated chemical reactions to produce at least two different reaction intermediates from templates associated with reactive units having the same chemical functionality (for example, an amine reactive group, an amide reactive group, a carboxylate reactive group, a sulfhydryl reactive group, or a hydroxyl reactive group); and (b) in a second, different solution, performing at least two different nucleic acid-mediated chemical reactions to produce at least two different reaction products from the at least two reaction intermediates, wherein the reaction products are associated with the templates that encoded their synthesis.

In this approach, the reactive units can be covalently attached to the templates. In addition or in the alternative, the reaction intermediates can be covalently attached to the templates that encoded their synthesis. In addition or in the alternative, the reaction products are covalently attached to the templates that encoded their synthesis.

Various aspects of nucleic acid-templated chemistry are discussed in detail below. Additional information may be found in U.S. Patent Application Publication Nos. 2004/0180412 A1 (U.S. Ser. No. 10/643,752) by Liu et al. and 2003/0113738 A1 (U.S. Ser. No. 10/101,030) by Liu et al., and in U.S. Patent Application Ser. No. 60/661,039 by Askenazi et al.

I. Template Considerations

The nucleic acid template can direct a wide variety of chemical reactions without obvious structural requirements by sequence-specifically recruiting reactants linked to complementary oligonucleotides. As discussed, the nucleic acid-mediated format permits reactions that may not be possible using conventional synthetic approaches. During synthesis, the template hybridizes or anneals to one or more transfer units to direct the synthesis of a reaction product, which during certain steps of templated synthesis remain associated with the template. A reaction product then is selected or screened based on certain criteria, such as the ability to bind to a preselected target molecule. Once the reaction product has been identified, the associated template can then be sequenced to decode the synthetic history of the reaction product. Furthermore, as will be discussed in more detail below, the template may be evolved to guide the synthesis of another chemical compound or library of chemical compounds.

(i) Template Format

The template may incorporate a hairpin loop on one end terminating in a reactive unit that can interact with one or more reactive units associated with transfer units. For example, a DNA template can comprise a hairpin loop terminating in a 5'-amino group, which may or may not be protected. The amino group may act as an initiation point for formation of an unnatural polymer or small molecule.

The length of the template may vary greatly depending upon the type of the nucleic acid-templated synthesis contemplated. For example, in certain embodiments, the template may be from 10 to 10,000 nucleotides in length, from 20 to 1,000 nucleotides in length, from 20 to 400 nucleotides in length, from 40 to 1,000 nucleotides in length, or from 40 to 400 nucleotides in length. The length of the template will of course depend on, for example, the length of the codons, the complexity of the library, the complexity and/or size of a reaction product, the use of spacer sequences, etc.

(ii) Codon Usage

It is contemplated that the sequence of the template may be designed in a number of ways without going beyond the scope of the present invention. For example, the length of the codon must be determined and the codon sequences must be set. If a codon length of two is used, then using the four naturally occurring bases only 16 possible combinations are available to be used in encoding the library. If the length of the codon is increased to three (the number Nature uses in encoding proteins), the number of possible combinations increases to 64. If the length of the codon is increased to four, the number of possible combinations increases to 256. Other factors to be considered in determining the length of the codon are mismatching, frame-shifting, complexity of library, etc. As the length of the codon is increased up to a certain point the number of mismatches is decreased; however, excessively long codons likely will hybridize despite mismatched base pairs.

Although the length of the codons may vary, the codons may range from 2 to 50 nucleotides, from 2 to 40 nucleotides, from 2 to 30 nucleotides, from 2 to 20 nucleotides, from 2 to 15 nucleotides, from 2 to 10 nucleotides, from 3 to 50 nucleotides, from 3 to 40 nucleotides, from 3 to 30 nucleotides, from 3 to 20 nucleotides, from 3 to 15 nucleotides, from 3 to 10 nucleotides, from 4 to 50 nucleotides, from 4 to 40 nucleotides, from 4 to 30 nucleotides, from 4 to 20 nucleotides, from 4 to 15 nucleotides, from 4 to 10 nucleotides, from 5 to 50 nucleotides, from 5 to 40 nucleotides, from 5 to 30 nucleotides, from 5 to 20 nucleotides, from 5 to 15 nucleotides, from 5 to 10 nucleotides, from 6 to 50 nucleotides, from 6 to 40 nucleotides, from 6 to 30 nucleotides, from 6 to 20 nucleotides, from 6 to 15 nucleotides, from 6 to 10 nucleotides, from 7 to 50 nucleotides, from 7 to 40 nucleotides, from 7 to 30 nucleotides, from 7 to 20 nucleotides, from 7 to 15 nucleotides, from 7 to 10 nucleotides, from 8 to 50 nucleotides, from 8 to 40 nucleotides, from 8 to 30 nucleotides, from 8 to 20 nucleotides, from 8 to 15 nucleotides, from 8 to 10 nucleotides, from 9 to 50 nucleotides, from 9 to 40 nucleotides, from 9 to 30 nucleotides, from 9 to 20 nucleotides, from 9 to 15 nucleotides, from 9 to 10 nucleotides. Codons, however, preferably are 3, 4, 5, 6, 7, 8, 9 or 10 nucleotides in length.

In one embodiment, the set of codons used in the template maximizes the number of mismatches between any two codons within a codon set to ensure that only the proper anti-codons of the transfer units anneal to the codon sites of the template. Furthermore, it is important that the template has mismatches between all the members of one codon set and all the codons of a different codon set to ensure that the anti-codons do not inadvertently bind to the wrong codon set. For example, with regard to the choice of codons n bases in length, each of the codons within a particular codon set should differ with one another by k mismatches, and all of the codons in one codon set should differ by m mismatches with all of the codons in the other codon set. Exemplary values for n, k, and m, for a variety of codon sets suitable for use on a template are published, for example, in Table 1 of U.S. Patent Application Publication No. US-2004/0180412, by Liu et al.

Using an appropriate algorithm, it is possible to generate sets of codons that maximize mismatches between any two codons within the same set, where the codons are n bases long having at least k mismatches between any two codons. Since between any two codons, there must be at least k mismatches, any two subcodons of n−(k−1) bases must have at least one mismatch. This sets an upper limit of $4^{n-k+1}$ on the size of any (n, k) codon set. Such an algorithm preferably starts with the $4^{n-k+1}$ possible subcodons of length n−(k−1) and then tests all combinations of adding k−1 bases for those that always maintain k mismatches. All possible (n, k) sets can be generated for n≦6. For n>6, the $4^{n-k+1}$ upper limits of codons cannot be met and a "full" packing of viable codons is mathematically impossible. In addition to there being at least one mismatch k between codons within the same codon set, there should also be at least one mismatch m between all the codons of one codon set and all the codons of another codon set. Using this approach, different sets of codons can be generated so that no codons are repeated.

By way of example, four (n=5, k=3, m=1) sets, each with 64 codons, can be chosen that always have at least one mismatch between any two codons in different sets and at least three mismatches between codons in the same set, as described, for example, in Tables 2-5 of U.S. Patent Application Publication No. US-2004/0180412, by Liu et al. Similarly, four (n=6, k=4, m=2) sets, each with 64 codons, can be chosen that always have at least two mismatches between any two codons in different codon sets and at least four mismatches between codons in the same codon set as described, for example, in Tables 6-9 of U.S. Patent Application Publication No. US-2004/0180412, by Liu et al.

Codons can also be chosen to increase control over the GC content and, therefore, the melting temperature of the codon and anti-codon. Codons sets with a wide range in GC content versus AT content may result in reagents that anneal with different efficiencies due to different melting temperatures.

By screening for GC content among different (n, k) sets, the GC content for the codon sets can be optimized. For example, the four (6, 4, 2) codon sets set forth in Tables 6-9 each contain 40 codons with identical GC content (i.e., 50% GC content). By using only these 40 codons at each position, all the reagents in theory will have comparable melting temperatures, removing potential biases in annealing that might otherwise affect library synthesis. Longer codons that maintain a large number of mismatches such as those appropriate for certain applications such as the reaction discovery system can also be chosen using this approach. For example, by combining two (6, 4) sets together while matching low GC to high GC codons, (12, 8) sets with 64 codons all with 50% GC content can be generated for use in reaction discovery selections as well as other application where multiple mismatches might be advantageous. These codons satisfy the requirements for encoding a 30×30 matrix of functional group combinations for reaction discovery.

Although an anti-codon is intended to bind only to a codon, an anti-codon may also bind to an unintended sequence on a template if complementary sequence is present. Thus, an anti-codon may inadvertently bind to a non-codon sequence. Alternatively, an anti-codon might inadvertently bind out-of-frame by annealing in part to one codon and in part to another codon or to a non-codon sequence. Finally, an anti-codon might bind in-frame to an incorrect codon, an issue addressed by the codon sets described above by requiring at least one base difference distinguishing each codon. In Nature, the problems of noncoding sequences and out-of-frame binding are avoided by the ribosome. The nucleic acid-templated methods described herein, however, do not take advantage of the ribosome's fidelity. Therefore, in order to avoid erroneous annealing, the templates can be designed such that sequences complementary to anti-codons are found exclusively at in-frame codon positions. For example, codons can be designed to begin, or end, with a particular base (e.g., "G"). If that base is omitted from all other positions in the template (i.e., all other positions are restricted to T, C, and A), only perfect codon sequences in the template will be at the in-frame codon sequences. Similarly, the codon may be designed to be sufficiently long such that its sequence is unique and does not appear elsewhere in a template.

When the nucleic acid-templated synthesis is used to produce a polymer or a small molecule, spacer sequences may also be placed between the codons to prevent frame shifting. For example, the bases of the template that encode a polymer subunit (the "genetic code" for the polymer) may be chosen from Table 1 to preclude or minimize the possibility of out-of-frame annealing. These genetic codes reduce undesired frameshifted nucleic acid-templated polymer translation and differ in the range of expected melting temperatures and in the minimum number of mismatches that result during out-of-frame annealing.

TABLE 1

Representative Genetic Codes for Nucleic Acid-templated Polymers That Preclude Out-Of-Frame Annealing

| Sequence | Number of Possible Codons |
| --- | --- |
| VVNT | 36 possible codons |
| NVVT | 36 possible codons |
| SSWT | 8 possible codons |
| SSST | 8 possible codons |
| SSNT | 16 possible codons |
| VNVNT or NVNVT | 144 possible codons |
| SSSWT or SSWST | 16 possible codons |
| SNSNT or NSNST | 64 possible codons |
| SSNWT or SWNST | 32 possible codons |
| WSNST or NSWST | 32 possible codons | where, V=A, C, or G, S=C or G, W=A or T, and N=A, C, G, or T

As in Nature, start and stop codons are useful, particularly in the context of polymer synthesis, to restrict erroneous anti-codon annealing to non-codons and to prevent excessive extension of a growing polymer. For example, a start codon can anneal to a transfer unit bearing a small molecule scaffold or a start monomer unit for use in polymer synthesis; the start monomer unit can be masked by a photolabile protecting group. A stop codon, if used to terminate polymer synthesis, should not conflict with any other codons used in the synthesis and should be of the same general format as the other codons. Generally, a stop codon can encode a monomer unit that terminates polymerization by not providing a reactive group for further attachment. For example, a stop monomer unit may contain a blocked reactive group such as an acetamide rather than a primary amine. In other embodiments, the stop monomer unit can include a biotinylated terminus that terminates the polymerization and facilitates purification of the resulting polymer.

(iii) Template Synthesis

The templates may be synthesized using methodologies well known in the art. For example, the nucleic acid sequence may be prepared using any method known in the art to prepare nucleic acid sequences. These methods include both in vivo and in vitro methods including PCR, plasmid preparation, endonuclease digestion, solid phase synthesis (for example, using an automated synthesizer), in vitro transcription, strand separation, etc. Following synthesis, the template, when desired may be associated (for example, covalently or non covalently coupled) with a reactive unit of interest using standard coupling chemistries known in the art.

An efficient method to synthesize a large variety of templates is to use a "split-pool" technique. The oligonucleotides are synthesized using standard 3' to 5' chemistries. First, the constant 3' end is synthesized. This is then split into n different vessels, where n is the number of different codons to appear at that position in the template. For each vessel, one of the n different codons is synthesized on the (growing) 5' end of the constant 3' end. Thus, each vessel contains, from 5' to 3', a different codon attached to a constant 3' end. The n vessels are then pooled, so that a single vessel contains n different codons attached to the constant 3' end. Any constant bases adjacent the 5' end of the codon are now synthesized. The pool then is split into m different vessels, where m is the number of different codons to appear at the next (more 5') position of the template. A different codon is synthesized (at the 5' end of the growing oligonucleotide) in each of the m vessels. The resulting oligonucleotides are pooled in a single vessel. Splitting, synthesizing, and pooling are repeated as required to synthesize all codons and constant regions in the oligonucleotides.

II. Transfer Units

A transfer unit comprises an oligonucleotide containing an anti-codon sequence and a reactive unit. The anti-codons are designed to be complementary to the codons present in the template. Accordingly, the sequences used in the template and the codon lengths should be considered when designing the anti-codons. Any molecule complementary to a codon used in the template may be used, including natural or non-natural nucleotides. In certain embodiments, the codons include one or more bases found in nature (i.e., thymidine, uracil, guanidine, cytosine, and adenine). Thus, the anti-codon can include one or more nucleotides normally found in Nature with a base, a sugar, and an optional phosphate group. Alternatively, the bases may be connected via a backbone other than the sugar-phosphate backbone normally found in Nature (e.g., non-natural nucleotides).

As discussed above, the anti-codon is associated with a particular type of reactive unit to form a transfer unit. The reactive unit may represent a distinct entity or may be part of the functionality of the anti-codon unit. In certain embodiments, each anti-codon sequence is associated with one monomer type. For example, the anti-codon sequence ATTAG may be associated with a carbamate residue with an isobutyl side chain, and the anti-codon sequence CATAG may be associated with a carbamate residue with a phenyl side chain. This one-for-one mapping of anti-codon to monomer units allows the decoding of any polymer of the library by sequencing the nucleic acid template used in the synthesis and allows synthesis of the same polymer or a related polymer by knowing the sequence of the original polymer. By changing (e.g., mutating) the sequence of the template, different monomer units may be introduced, thereby allowing the synthesis of related polymers, which can subsequently be selected and evolved. In certain preferred embodiments, several anti-codons may code for one monomer unit as is the case in Nature.

In certain other embodiments, where a small molecule library is to be created rather than a polymer library, the anti-codon generally is associated with a reactive unit or reactant used to modify a small molecule scaffold. In certain embodiments, the reactant is linked to the anti-codon via a linker long enough to allow the reactant to come into reactive proximity with the small molecule scaffold. The linker preferably has a length and composition to permit intramolecular reactions but yet minimize intermolecular reactions. The reactants include a variety of reagents as demonstrated by the wide range of reactions that can be utilized in nucleic acid-templated synthesis and can be any chemical group, catalyst (e.g., organometallic compounds), or reactive moiety (e.g., electrophiles, nucleophiles) known in the chemical arts.

Additionally, the association between the anti-codon and the reactive unit, for example, a monomer unit or reactant, in the transfer unit may be covalent or non-covalent. The association maybe through a covalent bond and, in certain embodiments, the covalent bond may be severable.

Thus, the anti-codon can be associated with the reactant through a linker moiety. The linkage can be cleavable by light, oxidation, hydrolysis, exposure to acid, exposure to base, reduction, etc. Fruchtel et al. (1996) ANGEW. CHEM. INT. ED. ENGL. 35: 17 describes a variety of linkages useful in the practice of the invention. The linker facilitates contact of the reactant with the small molecule scaffold and in certain embodiments, depending on the desired reaction, positions DNA as a leaving group ("autocleavable" strategy), or may link reactive groups to the template via the "scarless" linker strategy (which yields product without leaving behind an additional atom or atoms having chemical functionality), or a "useful scar" strategy (in which a portion of the linker is left behind to be functionalized in subsequent steps following linker cleavage).

With the "autocleavable" linker strategy, the DNA-reactive group bond is cleaved as a natural consequence of the reaction. In the "scarless" linker strategy, DNA-templated reaction of one reactive group is followed by cleavage of the linker attached through a second reactive group to yield products without leaving behind additional atoms capable of providing chemical functionality. Alternatively, a "useful scar" may be utilized on the theory that it may be advantageous to introduce useful atoms and/or chemical groups as a consequence of linker cleavage. In particular, a "useful scar" is left behind following linker cleavage and can be functionalized in subsequent steps.

The anti-codon and the reactive unit (monomer unit) may also be associated through non-covalent interactions such as ionic, electrostatic, hydrogen bonding, van der Waals interactions, hydrophobic interactions, pi-stacking, etc. and combinations thereof. To give but one example, an anti-codon may be linked to biotin, and a monomer unit linked to streptavidin. The propensity of streptavidin to bind biotin leads to the non-covalent association between the anti-codon and the monomer unit to form the transfer unit.

The specific annealing of transfer units to templates permits the use of transfer units at concentrations lower than concentrations used in many traditional organic syntheses. Thus, transfer units can be used at submillimolar concentrations (e.g. less than 100 µM, less than 10 µM, less than 1 µM, less than 100 nM, or less than 10 nM).

III. Chemical Reactions

A variety of compounds and/or libraries can be prepared using the methods described herein. In certain embodiments, compounds that are not, or do not resemble, nucleic acids or analogs thereof, are synthesized according to the method of the invention. In certain other embodiments, compounds that are not, or do not resemble, proteins, peptides, or analogs thereof, are synthesized according to the method of the invention.

(i) Coupling Reactions for Small Molecule Synthesis

In some embodiments, it is possible to create compounds such as small molecules using the methods described herein. These small molecules may be like natural products, non-polymeric, and/or non-oligomeric. The substantial interest in small molecules is due in part to their use as the active ingredient in many pharmaceutical preparations although they may also be used, for example, as catalysts, materials, or additives.

In synthesizing small molecules using the method of the present invention, an evolvable template also is provided. The template can include a small molecule scaffold upon which the small molecule is to be built, or a small molecule scaffold may be added to the template. The small molecule scaffold can be any chemical compound with two or more sites for functionalization. For example, the small molecule scaffold can include a ring system (e.g., the ABCD steroid ring system found in cholesterol) with functionalizable groups coupled to the atoms making up the rings. In another example, the small molecule may be the underlying structure of a pharmaceutical agent such as morphine, epothilone or a cephalosporin antibiotic. The sites or groups to be functionalized on the small molecule scaffold may be protected using methods and protecting groups known in the art. The protecting groups used in a small molecule scaffold may be orthogonal to one another so that protecting groups can be removed one at a time.

In this embodiment, the transfer units comprise an anti-codon associated with a reactant or a building block for use in modifying, adding to, or taking away from the small molecule scaffold. The reactants or building blocks may be, for example, electrophiles (e.g., acetyl, amides, acid chlorides, esters, nitrites, imines), nucleophiles (e.g., amines, hydroxyl groups, thiols), catalysts (e.g., organometallic catalysts), or side chains. The transfer units are allowed to contact the template under hydridizing conditions. As a result of oligonucleotide annealing, the attached reactant or building block is allowed to react with a site on the small molecule scaffold. In certain embodiments, protecting groups on the small molecule template are removed one at a time from the sites to be functionalized so that the reactant of the transfer unit will react at only the desired position on the scaffold.

The reaction conditions, linker, reactant, and site to be functionalized are chosen to avoid intermolecular reactions and accelerate intramolecular reactions. Sequential or simultaneous contacting of the template with transfer units can be employed depending on the particular compound to be synthesized. In certain embodiments of special interest, the multi-step synthesis of chemical compounds is provided in which the template is contacted sequentially with two or more transfer units to facilitate multi-step synthesis of complex chemical compounds.

After the sites on the scaffold have been modified, the newly synthesized small molecule remains associated with the template that encoded its synthesis. Decoding the sequence of the template permits the deconvolution of the synthetic history and thereby the structure of the small molecule. The template can also be amplified in order to create more of the desired small molecule and/or the template can be evolved (mutagenized) to create related small molecules. The small molecule can also be cleaved from the template for purification or screening.

(ii) Coupling Reactions for Polymer Synthesis

In certain embodiments, polymers, specifically unnatural polymers, are prepared according to the method of the present invention. The unnatural polymers that can be created using the inventive method and system include any unnatural polymers. Exemplary unnatural polymers include, but are not limited to, peptide nucleic acid (PNA) polymers, polycarbamates, polyureas, polyesters, polyacrylate, polyalkylene (e.g., polyethylene, polypropylene), polycarbonates, polypeptides with unnatural stereochemistry, polypeptides with unnatural amino acids, and combination thereof. In certain embodiments, the polymers comprise at least 10, 25, 75, 100, 125, 150 monomer units or more. The polymers synthesized using the inventive system may be used, for example, as catalysts, pharmaceuticals, metal chelators, or catalysts.

In preparing certain unnatural polymers, the monomer units attached to the anti-codons may be any monomers or oligomers capable of being joined together to form a polymer. The monomer units may be, for example, carbamates, D-amino acids, unnatural amino acids, PNAs, ureas, hydroxy acids, esters, carbonates, acrylates, or ethers. In certain embodiments, the monomer units have two reactive groups used to link the monomer unit into the growing polymer chain. Preferably, the two reactive groups are not the same so that the monomer unit may be incorporated into the polymer in a directional sense, for example, at one end may be an electrophile and at the other end a nucleophile. Reactive groups may include, but are not limited to, esters, amides, carboxylic acids, activated carbonyl groups, acid chlorides, amines, hydroxyl groups, and thiols. In certain embodiments, the reactive groups are masked or protected (Greene et al. (1999) PROTECTIVE GROUPS IN ORGANIC SYNTHESIS 3rd Edition, Wiley) so that polymerization may not take place until a desired time when the reactive groups are deprotected. Once the monomer units are assembled along the nucleic acid template, initiation of the polymerization sequence results in a cascade of polymerization and deprotection steps wherein the polymerization step results in deprotection of a reactive group to be used in the subsequent polymerization step.

The monomer units to be polymerized can include two or more monomers depending on the geometry along the nucleic acid template. The monomer units to be polymerized must be able to stretch along the nucleic acid template and particularly across the distance spanned by its encoding anti-codon and optional spacer sequence. In certain embodiments, the monomer unit actually comprises two monomers, for example, a dicarbamate, a diurea, or a dipeptide. In yet other embodiments, the monomer unit comprises three or more monomers.

The monomer units may contain any chemical groups known in the art. Reactive chemical groups especially those that would interfere with polymerization, hybridization, etc., are preferably masked using known protecting groups (Greene et al. (1999) supra). In general, the protecting groups used to mask these reactive groups are orthogonal to those used in protecting the groups used in the polymerization steps.

It has been discovered that, under certain circumstances, the type of chemical reaction may affect the fidelity of the polymerization process. For example, distance independent chemical reactions (for example, reactions that occur efficiently when the reactive units are spaced apart by intervening bases, for example, amine acylation reactions) may result in the spurious incorporation of the wrong monomers at a particular position of a polymer chain. In contrast, by choosing chemical reactions for template mediated syntheses that are distance dependent (for example, reactions that become inefficient the further the reactive units are spaced part via intervening bases, for example, reductive amination reactions), it is possible control the fidelity of the polymerization process.

(iii) Functional Group Transformations

Nucleic acid-templated synthesis can be used to effect functional group transformations that either (i) unmask or (ii) interconvert functionality used in coupling reactions. By exposing or creating a reactive group within a sequence-programmed subset of a library, nucleic acid-templated functional group interconversions permit the generation of library diversity by sequential unmasking. The sequential unmasking approach offers the major advantage of enabling reactants that would normally lack the ability to be linked to a nucleic acid (for example, simple alkyl halides) to contribute to library diversity by reacting with a sequence-specified subset of templates in an intermolecular, non-templated reaction mode. This advantage significantly increases the types of structures that can be generated.

One embodiment of the invention involves deprotection or unmasking of functional groups present in a reactive unit. According to this embodiment, a nucleic acid-template is associated with a reactive unit that contains a protected functional group. A transfer unit, comprising an oligonucleotide complimentary to the template codon region and a reagent capable of removing the protecting group, is annealed to the template, and the reagent reacts with the protecting group, removing it from the reactive unit. To further functionalize the reactive unit, the exposed functional group then is subjected to a reagent not linked to a nucleic acid. In some embodiments, the reactive unit contains two or more protected functional groups. In still other embodiments, the protecting groups are orthogonal protecting groups that are sequentially removed by iterated annealing with reagents linked to transfer units.

Another embodiment of the invention involves interconversions of functional groups present on a reactive unit. According to this embodiment, a transfer unit associated with a reagent that can catalyze a reaction is annealed to a template bearing the reactive unit. A reagent not linked to a nucleic acid is added to the reaction, and the transfer unit reagent catalyzes the reaction between the unlinked reagent and the reactive unit, yielding a newly functionalized reactive unit. In some embodiments, the reactive unit contains two or more functional groups which are sequentially interconverted by iterative exposure to different transfer unit-bound reagents.

(iv) Reaction Conditions

Nucleic acid-templated reactions can occur in aqueous or non-aqueous (i.e., organic) solutions, or a mixture of one or more aqueous and non-aqueous solutions. In aqueous solutions, reactions can be performed at pH ranges from about 2 to about 12, or preferably from about 2 to about 10, or more preferably from about 4 to about 10. The reactions used in DNA-templated chemistry preferably should not require very basic conditions (e.g., pH>12, pH>10) or very acidic conditions (e.g., pH<1, pH<2, pH<4), because extreme conditions may lead to degradation or modification of the nucleic acid template and/or molecule (for example, the polymer, or small molecule) being synthesized. The aqueous solution can contain one or more inorganic salts, including, but not limited to, NaCl, $Na_2SO_4$, KCl, $Mg^{+2}$, $Mn^{+2}$, etc., at various concentrations.

Organic solvents suitable for nucleic acid-templated reactions include, but are not limited to, methylene chloride, chloroform, dimethylformamide, and organic alcohols, including methanol and ethanol. To permit quantitative dissolution of reaction components in organic solvents, quaternized ammonium salts, such as, for example, long chain tetraalkylammonium salts, can be added (Jost et al. (1989) NUCLEIC ACIDS RES. 17: 2143; Mel'nikov et al. (1999) LANGMUIR 15: 1923-1928).

Nucleic acid-templated reactions may require a catalyst, such as, for example, homogeneous, heterogeneous, phase transfer, and asymmetric catalysis. In other embodiments, a catalyst is not required. The presence of additional, accessory reagents not linked to a nucleic acid are preferred in some embodiments. Useful accessory reagents can include, for example, oxidizing agents (e.g., $NaIO_4$); reducing agents (e.g., $NaCNBH_3$); activating reagents (e.g., EDC, NHS, and sulfo-NHS); transition metals such as nickel (e.g., $Ni(NO_3)_2$), rhodium (e.g. $RhCl_3$), ruthenium (e.g. $RuCl_3$), copper (e.g. $Cu(NO_3)_2$), cobalt (e.g. $CoCl_2$), iron (e.g. $Fe(NO_3)_3$), osmium (e.g. $OsO_4$), titanium (e.g. $TiCl_4$ or titanium tetraisopropoxide), palladium (e.g. $NaPdCl_4$), or Ln; transition metal ligands (e.g., phosphines, amines, and halides); Lewis acids; and Lewis bases.

Reaction conditions preferably are optimized to suit the nature of the reactive units and oligonucleotides used.

(v) Classes of Chemical Reactions

Known chemical reactions for synthesizing polymers, small molecules, or other molecules can be used in nucleic acid-templated reactions. Thus, reactions such as those listed in *March's Advanced Organic Chemistry, Organic Reactions, Organic Syntheses*, organic text books, journals such as *Journal of the American Chemical Society, Journal of Organic Chemistry, Tetrahedron*, etc., and Carruther's *Some Modern Methods of Organic Chemistry* can be used. The chosen reactions preferably are compatible with nucleic acids such as DNA or RNA or are compatible with the modified nucleic acids used as the template.

Reactions useful in nucleic-acid templated chemistry include, for example, substitution reactions, carbon-carbon bond forming reactions, elimination reactions, acylation reactions, and addition reactions. An illustrative but not exhaustive list of aliphatic nucleophilic substitution reactions useful in the present invention includes, for example, $S_N2$ reactions, $S_N1$ reactions, $S_Ni$ reactions, allylic rearrangements, nucleophilic substitution at an aliphatic trigonal carbon, and nucleophilic substation at a vinylic carbon.

Specific aliphatic nucleophilic substitution reactions with oxygen nucleophiles include, for example, hydrolysis of alkyl halides, hydrolysis of gen-dihalides, hydrolysis of 1,1,1-trihalides, hydrolysis of alkyl esters or inorganic acids, hydrolysis of diazo ketones, hydrolysis of acetal and enol ethers, hydrolysis of epoxides, hydrolysis of acyl halides, hydrolysis of anhydrides, hydrolysis of carboxylic esters, hydrolysis of amides, alkylation with alkyl halides (Williamson Reaction), epoxide formation, alkylation with inorganic esters, alkylation with diazo compounds, dehydration of alcohols, transetherification, alcoholysis of epoxides, alkylation with onium salts, hydroxylation of silanes, alcoholysis of acyl halides, alcoholysis of anhydrides, esterification of carboxylic acids, alcoholysis of carboxylic esters (transesterfication), alcoholysis of amides, alkylation of carboxylic acid salts, cleavage of ether with acetic anhydride, alkylation of carboxylic acids with diazo compounds, acylation of carboxylic acids with acyl halides, acylation of carboxylic acids with carboxylic acids, formation of oxonium salts, preparation of peroxides and hydroperoxides, preparation of inorganic esters (e.g., nitrites, nitrates, sulfonates), preparation of alcohols from amines, and preparation of mixed organic-inorganic anhydrides.

Specific aliphatic nucleophilic substitution reactions with sulfur nucleophiles, which tend to be better nucleophiles than their oxygen analogs, include, for example, attack by SH at an alkyl carbon to form thiols, attack by S at an alkyl carbon to form thioethers, attack by SH or SR at an acyl carbon, formation of disulfides, formation of Bunte salts, alkylation of sulfinic acid salts, and formation of alkyl thiocyanates.

Aliphatic nucleophilic substitution reactions with nitrogen nucleophiles include, for example, alkylation of amines, N-arylation of amines, replacement of a hydroxy by an amino group, transamination, transamidation, alkylation of amines with diazo compounds, amination of epoxides, amination of oxetanes, amination of aziridines, amination of alkanes, formation of isocyanides, acylation of amines by acyl halides, acylation of amines by anhydrides, acylation of amines by carboxylic acids, acylation of amines by carboxylic esters, acylation of amines by amides, acylation of amines by other acid derivatives, N-alkylation or N-arylation of amides and imides, N-acylation of amides and imides, formation of aziridines from epoxides, formation of nitro compounds, formation of azides, formation of isocyanates and isothiocyanates, and formation of azoxy compounds.

Aliphatic nucleophilic substitution reactions with halogen nucleophiles include, for example, attack at an alkyl carbon, halide exchange, formation of alkyl halides from esters of sulfuric and sulfonic acids, formation of alkyl halides from alcohols, formation of alkyl halides from ethers, formation of halohydrins from epoxides, cleavage of carboxylic esters with lithium iodide, conversion of diazo ketones to α-halo ketones, conversion of amines to halides, conversion of tertiary amines to cyanamides (the von Braun reaction), formation of acyl halides from carboxylic acids, and formation of acyl halides from acid derivatives.

Aliphatic nucleophilic substitution reactions using hydrogen as a nucleophile include, for example, reduction of alkyl halides, reduction of tosylates, other sulfonates, and similar compounds, hydrogenolysis of alcohols, hydrogenolysis of esters (Barton-McCombie reaction), hydrogenolysis of nitriles, replacement of alkoxyl by hydrogen, reduction of epoxides, reductive cleavage of carboxylic esters, reduction of a C—N bond, desulfurization, reduction of acyl halides, reduction of carboxylic acids, esters, and anhydrides to aldehydes, and reduction of amides to aldehydes.

Although certain carbon nucleophiles may be too nucleophilic and/or basic to be used in certain embodiments of the invention, aliphatic nucleophilic substitution reactions using carbon nucleophiles include, for example, coupling with silanes, coupling of alkyl halides (the Wurtz reaction), the reaction of alkyl halides and sulfonate esters with Group I (I A) and II (II A) organometallic reagents, reaction of alkyl halides and sulfonate esters with organocuprates, reaction of alkyl halides and sulfonate esters with other organometallic reagents, allylic and propargylic coupling with a halide substrate, coupling of organometallic reagents with esters of sulfuric and sulfonic acids, sulfoxides, and sulfones, coupling involving alcohols, coupling of organometallic reagents with carboxylic esters, coupling of organometallic reagents with compounds containing an ester linkage, reaction of organometallic reagents with epoxides, reaction of organometallics with aziridine, alkylation at a carbon bearing an active hydrogen, alkylation of ketones, nitriles, and carboxylic esters, alkylation of carboxylic acid salts, alkylation at a position α to a heteroatom (alkylation of 1,3-dithianes), alkylation of dihydro-1,3-oxazine (the Meyers synthesis of aldehydes, ketones, and carboxylic acids), alkylation with trialkylboranes, alkylation at an alkynyl carbon, preparation of nitriles, direct conversion of alkyl halides to aldehydes and ketones, conversion of alkyl halides, alcohols, or alkanes to carboxylic acids and their derivatives, the conversion of acyl halides to ketones with organometallic compounds, the conversion of anhydrides, carboxylic esters, or amides to ketones with organometallic compounds, the coupling of acyl halides, acylation at a carbon bearing an active hydrogen, acylation of carboxylic esters by carboxylic esters (the Claisen and Dieckmann condensation), acylation of ketones and nitriles with carboxylic esters, acylation of carboxylic acid salts, preparation of acyl cyanides, and preparation of diazo ketones, ketonic decarboxylation.

Reactions which involve nucleophilic attack at a sulfonyl sulfur atom may also be used in the present invention and include, for example, hydrolysis of sulfonic acid derivatives (attack by OH), formation of sulfonic esters (attack by OR), formation of sulfonamides (attack by nitrogen), formation of sulfonyl halides (attack by halides), reduction of sulfonyl chlorides (attack by hydrogen), and preparation of sulfones (attack by carbon).

Aromatic electrophilic substitution reactions may also be used in nucleotide-templated chemistry. Hydrogen exchange reactions are examples of aromatic electrophilic substitution reactions that use hydrogen as the electrophile. Aromatic electrophilic substitution reactions which use nitrogen electrophiles include, for example, nitration and nitro-de-hydrogenation, nitrosation of nitroso-de-hydrogenation, diazonium coupling, direct introduction of the diazonium group, and amination or amino-de-hydrogenation. Reactions of this type with sulfur electrophiles include, for example, sulfonation, sulfo-de-hydrogenation, halosulfonation, halosulfo-de-hydrogenation, sulfurization, and sulfonylation. Reactions using halogen electrophiles include, for example, halogenation, and halo-de-hydrogenation. Aromatic electrophilic substitution reactions with carbon electrophiles include, for example, Friedel-Crafts alkylation, alkylation, alkyl-de-hydrogenation, Friedel-Crafts arylation (the Scholl reaction), Friedel-Crafts acylation, formylation with disubstituted formamides, formylation with zinc cyanide and HCl (the Gatterman reaction), formylation with chloroform (the Reimer-Tiemann reaction), other formylations, formyl-de-hydrogenation, carboxylation with carbonyl halides, carboxylation with carbon dioxide (the Kolbe-Schmitt reaction), amidation with isocyanates, N-alkylcarbamoyl-de-hydrogenation, hydroxyalkylation, hydroxyalkyl-de-hydrogenation, cyclodehydration of aldehydes and ketones, haloalkylation, halo-de-hydrogenation, aminoalkylation, amidoalkylation, dialkylaminoalkylation, dialkylamino-de-hydrogenation, thioalkylation, acylation with nitriles (the Hoesch reaction), cyanation, and cyano-de-hydrogenation. Reactions using oxygen electrophiles include, for example, hydroxylation and hydroxy-de-hydrogenation.

Rearrangement reactions include, for example, the Fries rearrangement, migration of a nitro group, migration of a nitroso group (the Fischer-Hepp Rearrangement), migration of an arylazo group, migration of a halogen (the Orton rearrangement), migration of an alkyl group, etc. Other reaction on an aromatic ring include the reversal of a Friedel-Crafts alkylation, decarboxylation of aromatic aldehydes, decarboxylation of aromatic acids, the Jacobsen reaction, deoxygenation, desulfonation, hydro-de-sulfonation, dehalogenation, hydro-de-halogenation, and hydrolysis of organometallic compounds.

Aliphatic electrophilic substitution reactions are also useful. Reactions using the $S_E1$, $S_E2$ (front), $S_E2$ (back), $S_Ei$, addition-elimination, and cyclic mechanisms can be used in the present invention. Reactions of this type with hydrogen as the leaving group include, for example, hydrogen exchange (deuterio-de-hydrogenation, deuteriation), migration of a double bond, and keto-enol tautomerization. Reactions with halogen electrophiles include, for example, halogenation of aldehydes and ketones, halogenation of carboxylic acids and acyl halides, and halogenation of sulfoxides and sulfones. Reactions with nitrogen electrophiles include, for example, aliphatic diazonium coupling, nitrosation at a carbon bearing an active hydrogen, direct formation of diazo compounds, conversion of amides to α-azido amides, direct amination at an activated position, and insertion by nitrenes. Reactions with sulfur or selenium electrophiles include, for example, sulfenylation, sulfonation, and selenylation of ketones and carboxylic esters. Reactions with carbon electrophiles include, for example, acylation at an aliphatic carbon, conversion of aldehydes to β-keto esters or ketones, cyanation, cyano-de-hydrogenation, alkylation of alkanes, the Stork enamine reaction, and insertion by carbenes. Reactions with metal electrophiles include, for example, metalation with organometallic compounds, metalation with metals and strong bases, and conversion of enolates to silyl enol ethers. Aliphatic electrophilic substitution reactions with metals as leaving groups include, for example, replacement of metals by hydrogen, reactions between organometallic reagents and oxygen, reactions between organometallic reagents and peroxides, oxidation of trialkylboranes to borates, conversion of Grignard reagents to sulfur compounds, halo-de-metalation, the conversion of organometallic compounds to amines, the conversion of organometallic compounds to ketones, aldehydes, carboxylic esters and amides, cyano-de-metalation, transmetalation with a metal, transmetalation with a metal halide, transmetalation with an organometallic compound, reduction of alkyl halides, metallo-de-halogenation, replacement of a halogen by a metal from an organometallic compound, decarboxylation of aliphatic acids, cleavage of alkoxides, replacement of a carboxyl group by an acyl group, basic cleavage of β-keto esters and β-diketones, haloform reaction, cleavage of non-enolizable ketones, the Haller-Bauer reaction, cleavage of alkanes, decyanation, and hydro-de-cyanation. Electrophlic substitution reactions at nitrogen include, for example, diazotization, conversion of hydrazines to azides, N-nitrosation, N-nitroso-de-hydrogenation, conversion of amines to azo compounds, N-halogenation, N-halo-de-hydrogenation, reactions of amines with carbon monoxide, and reactions of amines with carbon dioxide.

Aromatic nucleophilic substitution reactions may also be used in the present invention. Reactions proceeding via the $S_NAr$ mechanism, the $S_N1$ mechanism, the benzyne mechanism, the $S_{RN}1$ mechanism, or other mechanism, for example, can be used. Aromatic nucleophilic substitution reactions with oxygen nucleophiles include, for example, hydroxy-de-halogenation, alkali fusion of sulfonate salts, and replacement of OR or OAr. Reactions with sulfur nucleophiles include, for example, replacement by SH or SR. Reactions using nitrogen nucleophiles include, for example, replacement by $NH_2$, NHR, or $NR_2$, and replacement of a hydroxy group by an amino group. Reactions with halogen nucleophiles include, for example, the introduction halogens. Aromatic nucleophilic substitution reactions with hydrogen as the nucleophile include, for example, reduction of phenols and phenolic esters and ethers, and reduction of halides and nitro compounds. Reactions with carbon nucleophiles include, for example, the Rosenmund-von Braun reaction, coupling of organometallic compounds with aryl halides, ethers, and carboxylic esters, arylation at a carbon containing an active hydrogen, conversions of aryl substrates to carboxylic acids, their derivatives, aldehydes, and ketones, and the Ullmann reaction. Reactions with hydrogen as the leaving group include, for example, alkylation, arylation, and amination of nitrogen heterocycles. Reactions with $N_2^+$ as the leaving group include, for example, hydroxy-de-diazoniation, replacement by sulfur-containing groups, iodo-de-diazoniation, and the Schiemann reaction. Rearrangement reactions include, for example, the von Richter rearrangement, the Sommelet-Hauser rearrangement, rearrangement of aryl hydroxylamines, and the Smiles rearrangement.

Reactions involving free radicals can also be used, although the free radical reactions used in nucleotide-templated chemistry should be carefully chosen to avoid modification or cleavage of the nucleotide template. With that limitation, free radical substitution reactions can be used in the present invention. Particular free radical substitution reactions include, for example, substitution by halogen, halogenation at an alkyl carbon, allylic halogenation, benzylic halogenation, halogenation of aldehydes, hydroxylation at an aliphatic carbon, hydroxylation at an aromatic carbon, oxidation of aldehydes to carboxylic acids, formation of cyclic ethers, formation of hydroperoxides, formation of peroxides, acyloxylation, acyloxy-de-hydrogenation, chlorosulfonation, nitration of alkanes, direct conversion of aldehydes to amides, amidation and amination at an alkyl carbon, simple coupling at a susceptible position, coupling of alkynes, arylation of aromatic compounds by diazonium salts, arylation of activated alkenes by diazonium salts (the Meerwein arylation), arylation and alkylation of alkenes by organopalladium compounds (the Heck reaction), arylation and alkylation of alkenes by vinyltin compounds (the Stille reaction), alkylation and arylation of aromatic compounds by peroxides, photochemical arylation of aromatic compounds, alkylation, acylation, and carbalkoxylation of nitrogen heterocycles Particular reactions in which $N_2^+$ is the leaving group include, for example, replacement of the diazonium group by hydrogen, replacement of the diazonium group by chlorine or bromine, nitro-de-diazoniation, replacement of the diazonium group by sulfur-containing groups, aryl dimerization with diazonium salts, methylation of diazonium salts, vinylation of diazonium salts, arylation of diazonium salts, and conversion of diazonium salts to aldehydes, ketones, or carboxylic acids. Free radical substitution reactions with metals as leaving groups include, for example, coupling of Grignard reagents, coupling of boranes, and coupling of other organometallic reagents. Reaction with halogen as the leaving group are included. Other free radical substitution reactions with various leaving groups include, for example, desulfurization with Raney Nickel, conversion of sulfides to organolithium compounds, decarboxylative dimerization (the Kolbe reaction), the Hunsdiecker reaction, decarboxylative allylation, and decarbonylation of aldehydes and acyl halides.

Reactions involving additions to carbon-carbon multiple bonds are also used in nucleotide-templated chemistry. Any mechanism may be used in the addition reaction including, for example, electrophilic addition, nucleophilic addition, free radical addition, and cyclic mechanisms. Reactions involving additions to conjugated systems can also be used. Addition to cyclopropane rings can also be utilized. Particular reactions include, for example, isomerization, addition of hydrogen halides, hydration of double bonds, hydration of triple bonds, addition of alcohols, addition of carboxylic acids, addition of $H_2S$ and thiols, addition of ammonia and amines, addition of amides, addition of hydrazoic acid, hydrogenation of double and triple bonds, other reduction of double and triple bonds, reduction of the double and triple bonds of conjugated systems, hydrogenation of aromatic rings, reductive cleavage of cyclopropanes, hydroboration, other hydrometalations, addition of alkanes, addition of alkenes and/or alkynes to alkenes and/or alkynes (e.g., pi-cation cyclization reactions, hydro-alkenyl-addition), ene reactions, the Michael reaction, addition of organometallics to double and triple bonds not conjugated to carbonyls, the addition of two alkyl groups to an alkyne, 1,4-addition of organometallic compounds to activated double bonds, addition of boranes to activated double bonds, addition of tin and mercury hydrides to activated double bonds, acylation of activated double bonds and of triple bonds, addition of alcohols, amines, carboxylic esters, aldehydes, etc., carbonylation of double and triple bonds, hydrocarboxylation, hydroformylation, addition of aldehydes, addition of HCN, addition of silanes, radical addition, radical cyclization, halogenation of double and triple bonds (addition of halogen, halogen), halolactonization, halolactamization, addition of hypohalous acids and hypohalites (addition of halogen, oxygen), addition of sulfur compounds (addition of halogen, sulfur), addition of halogen and an amino group (addition of halogen, nitrogen), addition of NOX and $NO_2X$ (addition of halogen, nitrogen), addition of $XN_3$ (addition of halogen, nitrogen), addition of alkyl halides (addition of halogen, carbon), addition of acyl halides (addition of halogen, carbon), hydroxylation (addition of oxygen, oxygen) (e.g., asymmetric dihydroxylation reaction with $OsO_4$), dihydroxylation of aromatic rings, epoxidation (addition of oxygen, oxygen) (e.g., Sharpless asymmetric epoxidation), photooxidation of dienes (addition of oxygen, oxygen), hydroxysulfenylation (addition of oxygen, sulfur), oxyamination (addition of oxygen, nitrogen), diamination (addition of nitrogen, nitrogen), formation of aziridines (addition of nitrogen), aminosulfenylation (addition of nitrogen, sulfur), acylacyloxylation and acylamidation (addition of oxygen, carbon or nitrogen, carbon), 1,3-dipolar addition (addition of oxygen, nitrogen, carbon), Diels-Alder reaction, heteroatom Diels-Alder reaction, all carbon 3+2 cycloadditions, dimerization of alkenes, the addition of carbenes and carbenoids to double and triple bonds, trimerization and tetramerization of alkynes, and other cycloaddition reactions.

In addition to reactions involving additions to carbon-carbon multiple bonds, addition reactions to carbon-hetero multiple bonds can be used in nucleotide-templated chemistry.

Exemplary reactions include, for example, the addition of water to aldehydes and ketones (formation of hydrates), hydrolysis of carbon-nitrogen double bond, hydrolysis of aliphatic nitro compounds, hydrolysis of nitriles, addition of alcohols and thiols to aldehydes and ketones, reductive alkylation of alcohols, addition of alcohols to isocyanates, alcoholysis of nitriles, formation of xanthates, addition of $H_2S$ and thiols to carbonyl compounds, formation of bisulfite addition products, addition of amines to aldehydes and ketones, addition of amides to aldehydes, reductive alkylation of ammonia or amines, the Mannich reaction, the addition of amines to isocyanates, addition of ammonia or amines to nitriles, addition of amines to carbon disulfide and carbon dioxide, addition of hydrazine derivative to carbonyl compounds, formation of oximes, conversion of aldehydes to nitriles, formation of gem-dihalides from aldehydes and ketones, reduction of aldehydes and ketones to alcohols, reduction of the carbon-nitrogen double bond, reduction of nitriles to amines, reduction of nitriles to aldehydes, addition of Grignard reagents and organolithium reagents to aldehydes and ketones, addition of other organometallics to aldehydes and ketones, addition of trialkylallylsilanes to aldehydes and ketones, addition of conjugated alkenes to aldehydes (the Baylis-Hillman reaction), the Reformatsky reaction, the conversion of carboxylic acid salts to ketones with organometallic compounds, the addition of Grignard reagents to acid derivatives, the addition of organometallic compounds to $CO_2$ and $CS_2$, addition of organometallic compounds to C=N compounds, addition of carbenes and diazoalkanes to C=N compounds, addition of Grignard reagents to nitriles and isocyanates, the Aldol reaction, Mukaiyama Aldol and related reactions, Aldol-type reactions between carboxylic esters or amides and aldehydes or ketones, the Knoevenagel reaction (e.g., the Nef reaction, the Favorskii reaction), the Peterson alkenylation reaction, the addition of active hydrogen compounds to $CO_2$ and $CS_2$, the Perkin reaction, Darzens glycidic ester condensation, the Tollens' reaction, the Wittig reaction, the Tebbe alkenylation, the Petasis alkenylation, alternative alkenylations, the Thorpe reaction, the Thorpe-Ziegler reaction, addition of silanes, formation of cyanohydrins, addition of HCN to C=N and C=N bonds, the Prins reaction, the benzoin condensation, addition of radicals to C=O, C=S, C=N compounds, the Ritter reaction, acylation of aldehydes and ketones, addition of aldehydes to aldehydes, the addition of isocyanates to isocyanates (formation of carbodiimides), the conversion of carboxylic acid salts to nitriles, the formation of epoxides from aldehydes and ketones, the formation of episulfides and episulfones, the formation of β-lactones and oxetanes (e.g., the Paterno-Büchi reaction), the formation of β-lactams, etc. Reactions involving addition to isocyanides include the addition of water to isocyanides, the Passerini reaction, the Ug reaction, and the formation of metalated aldimines.

Elimination reactions, including α, β, and γ eliminations, as well as extrusion reactions, can be performed using nucleotide-templated chemistry, although the strength of the reagents and conditions employed should be considered. Preferred elimination reactions include reactions that go by E1, E2, E1cB, or E2C mechanisms. Exemplary reactions include, for example, reactions in which hydrogen is removed from one side (e.g., dehydration of alcohols, cleavage of ethers to alkenes, the Chugaev reaction, ester decomposition, cleavage of quarternary ammonium hydroxides, cleavage of quaternary ammonium salts with strong bases, cleavage of amine oxides, pyrolysis of keto-ylids, decomposition of toluene-p-solfonylhydrazones, cleavage of sulfoxides, cleavage of selenoxides, cleavage of sulfornes, dehydrogalogenation of alkyl halides, dehydrohalogenation of acyl halides, dehydrohalogenation of sulfonyl halides, elimination of boranes, conversion of alkenes to alkynes, decarbonylation of acyl halides), reactions in which neither leaving atom is hydrogen (e.g., deoxygenation of vicinal diols, cleavage of cyclic thionocarbonates, conversion of epoxides to episulfides and alkenes, the Ramberg-Bäcklund reaction, conversion of aziridines to alkenes, dehalogenation of vicinal dihalides, dehalogenation of α-halo acyl halides, and elimination of a halogen and a hetero group), fragmentation reactions (i.e., reactions in which carbon is the positive leaving group or the electrofuge, such as, for example, fragmentation of γ-amino and γ-hydroxy halides, fragmentation of 1,3-diols, decarboxylation of β-hydroxy carboxylic acids, decarboxylation of β-lactones, fragmentation of α,β-epoxy hydrazones, elimination of CO from bridged bicyclic compounds, and elimination of $CO_2$ from bridged bicyclic compounds), reactions in which C=N or C=N bonds are formed (e.g., dehydration of aldoximes or similar compounds, conversion of ketoximes to nitriles, dehydration of unsubstituted amides, and conversion of N-alkylformamides to isocyanides), reactions in which C=O bonds are formed (e.g., pyrolysis of β-hydroxy alkenes), and reactions in which N=N bonds are formed (e.g., eliminations to give diazoalkenes). Extrusion reactions include, for example, extrusion of $N_2$ from pyrazolines, extrusion of $N_2$ from pyrazoles, extrusion of $N_2$ from triazolines, extrusion of CO, extrusion of $CO_2$, extrusion of $SO_2$, the Story synthesis, and alkene synthesis by twofold extrusion.

Rearrangements, including, for example, nucleophilic rearrangements, electrophilic rearrangements, prototropic rearrangements, and free-radical rearrangements, can also be performed using nucleotide-templated chemistry. Both 1,2 rearrangements and non-1,2 rearrangements can be performed. Exemplary reactions include, for example, carbon-to-carbon migrations of R, H, and Ar (e.g., Wagner-Meerwein and related reactions, the Pinacol rearrangement, ring expansion reactions, ring contraction reactions, acid-catalyzed rearrangements of aldehydes and ketones, the dienone-phenol rearrangement, the Favorskii rearrangement, the Arndt-Eistert synthesis, homologation of aldehydes, and homologation of ketones), carbon-to-carbon migrations of other groups (e.g., migrations of halogen, hydroxyl, amino, etc.; migration of boron; and the Neber rearrangement), carbon-to-nitrogen migrations of R and Ar (e.g., the Hofmann rearrangement, the Curtius rearrangement, the Lossen rearrangement, the Schmidt reaction, the Beckman rearrangement, the Stieglits rearrangement, and related rearrangements), carbon-to-oxygen migrations of R and Ar (e.g., the Baeyer-Villiger rearrangement and rearrangement of hydroperoxides), nitrogen-to-carbon, oxygen-to-carbon, and sulfur-to-carbon migration (e.g., the Stevens rearrangement, and the Wittig rearrangement), boron-to-carbon migrations (e.g., conversion of boranes to alcohols (primary or otherwise), conversion of boranes to aldehydes, conversion of boranes to carboxylic acids, conversion of vinylic boranes to alkenes, formation of alkynes from boranes and acetylides, formation of alkenes from boranes and acetylides, and formation of ketones from boranes and acetylides), electrocyclic rearrangements (e.g., of cyclobutenes and 1,3-cyclohexadienes, or conversion of stilbenes to phenanthrenes), sigmatropic rearrangements (e.g., (1,j) sigmatropic migrations of hydrogen, (1,j) sigmatropic migrations of carbon, conversion of vinylcyclopropanes to cyclopentenes, the Cope rearrangement, the Claisen rearrangement, the Fischer indole synthesis, (2,3) sigmatropic rearrangements, and the benzidine rearrangement), other cyclic rearrangements (e.g., metathesis of alkenes, the di-π-methane and related rearrangements, and the Hofmann-Löf- fler and related reactions), and non-cyclic rearrangements (e.g., hydride shifts, the Chapman rearrangement, the Wallach rearrangement, and dyotropic rearrangements).

Oxidative and reductive reactions may also be performed using nucleotide-templated chemistry. Exemplary reactions may involve, for example, direct electron transfer, hydride transfer, hydrogen-atom transfer, formation of ester intermediates, displacement mechanisms, or addition-elimination mechanisms. Exemplary oxidations include, for example, eliminations of hydrogen (e.g., aromatization of six-membered rings, dehydrogenations yielding carbon-carbon double bonds, oxidation or dehydrogenation of alcohols to aldehydes and ketones, oxidation of phenols and aromatic amines to quinones, oxidative cleavage of ketones, oxidative cleavage of aldehydes, oxidative cleavage of alcohols, ozonolysis, oxidative cleavage of double bonds and aromatic rings, oxidation of aromatic side chains, oxidative decarboxylation, and bisdecarboxylation), reactions involving replacement of hydrogen by oxygen (e.g., oxidation of methylene to carbonyl, oxidation of methylene to OH, $CO_2R$, or OR, oxidation of arylmethanes, oxidation of ethers to carboxylic esters and related reactions, oxidation of aromatic hydrocarbons to quinones, oxidation of amines or nitro compounds to aldehydes, ketones, or dihalides, oxidation of primary alcohols to carboxylic acids or carboxylic esters, oxidation of alkenes to aldehydes or ketones, oxidation of amines to nitroso compounds and hydroxylamines, oxidation of primary amines, oximes, azides, isocyanates, or notroso compounds, to nitro compounds, oxidation of thiols and other sulfur compounds to sulfonic acids), reactions in which oxygen is added to the substrate (e.g., oxidation of alkynes to α-diketones, oxidation of tertiary amines to amine oxides, oxidation of thioesters to sulfoxides and sulfones, and oxidation of carboxylic acids to peroxy acids), and oxidative coupling reactions (e.g., coupling involving carbanoins, dimerization of silyl enol ethers or of lithium enolates, and oxidation of thiols to disulfides).

Exemplary reductive reactions include, for example, reactions involving replacement of oxygen by hydrogen (e.g., reduction of carbonyl to methylene in aldehydes and ketones, reduction of carboxylic acids to alcohols, reduction of amides to amines, reduction of carboxylic esters to ethers, reduction of cyclic anhydrides to lactones and acid derivatives to alcohols, reduction of carboxylic esters to alcohols, reduction of carboxylic acids and esters to alkanes, complete reduction of epoxides, reduction of nitro compounds to amines, reduction of nitro compounds to hydroxylamines, reduction of nitroso compounds and hydroxylamines to amines, reduction of oximes to primary amines or aziridines, reduction of azides to primary amines, reduction of nitrogen compounds, and reduction of sulfonyl halides and sulfonic acids to thiols), removal of oxygen from the substrate (e.g., reduction of amine oxides and azoxy compounds, reduction of sulfoxides and sulfones, reduction of hydroperoxides and peroxides, and reduction of aliphatic nitro compounds to oximes or nitriles), reductions that include cleavage (e.g., de-alkylation of amines and amides, reduction of azo, azoxy, and hydrazo compounds to amines, and reduction of disulfides to thiols), reductive couplic reactions (e.g., bimolecular reduction of aldehydes and ketones to 1,2-diols, bimolecular reduction of aldehydes or ketones to alkenes, acyloin ester condensation, reduction of nitro to azoxy compounds, and reduction of nitro to azo compounds), and reductions in which an organic substrate is both oxidized and reduced (e.g., the Cannizzaro reaction, the Tishchenko reaction, the Pummerer rearrangement, and the Willgerodt reaction).

IV. Selection and Screening

Selection and/or screening for reaction products with desired activities (such as catalytic activity, binding affinity, or a particular effect in an activity assay) may be performed using methodologies known and used in the art. For example, affinity selections may be performed according to the principles used in library-based selection methods such as phage display, polysome display, and mRNA-fusion protein displayed peptides. Selection for catalytic activity may be performed by affinity selections on transition-state analog affinity columns (Baca et al. (1997) PROC. NATL. ACAD. SCI. USA 94(19): 10063-8) or by function-based selection schemes (Pedersen et al. (1998) PROC. NATL. ACAD. SCI. USA 95(18): 10523-8). Since minute quantities of DNA ($\sim 10^{-20}$ mol) can be amplified by PCR (Kramer et al. (1999) CURRENT PROTOCOLS IN MOLECULAR BIOLOGY (ed. Ausubel, F. M.) 15.1-15.3, Wiley), these selections can be conducted on a scale ten or more orders of magnitude less than that required for reaction analysis by current methods, making a truly broad search both economical and efficient.

(i) Selection for Binding to Target Molecule

The templates and reaction products can be selected (or screened) for binding to a target molecule. In this context, selection or partitioning means any process whereby a library member bound to a target molecule is separated from library members not bound to target molecules. Selection can be accomplished by various methods known in the art.

The templates of the present invention contain a built-in function for direct selection and amplification. In most applications, binding to a target molecule preferably is selective, such that the template and the resulting reaction product bind preferentially with a specific target molecule, perhaps preventing or inducing a specific biological effect. Ultimately, a binding molecule identified using the present invention may be useful as a therapeutic and/or diagnostic agent. Once the selection is complete, the selected templates optionally can be amplified and sequenced. The selected reaction products, if present in sufficient quantity, can be separated from the templates, purified (e.g., by HPLC, column chromatography, or other chromatographic method), and further characterized.

(ii) Target Molecules

Binding assays provide a rapid means for isolating and identifying reaction products that bind to, for example, a surface (such as metal, plastic, composite, glass, ceramics, rubber, skin, or tissue); a polymer; a catalyst; or a target biomolecule such as a nucleic acid, a protein (including enzymes, receptors, antibodies, and glycoproteins), a signal molecule (such as cAMP, inositol triphosphate, peptides, or prostaglandins), a carbohydrate, or a lipid. Binding assays can be advantageously combined with activity assays for the effect of a reaction product on a function of a target molecule.

The selection strategy can be carried out to allow selection against almost any target. Importantly, the selection strategy does not require any detailed structural information about the target molecule or about the molecules in the libraries. The entire process is driven by the binding affinity involved in the specific recognition and binding of the molecules in the library to a given target. Examples of various selection procedures are described below.

The libraries of the present invention can contain molecules that could potentially bind to any known or unknown target. The binding region of a target molecule could include a catalytic site of an enzyme, a binding pocket on a receptor (for example, a G-protein coupled receptor), a protein surface area involved in a protein-protein or protein-nucleic acid interaction (preferably a hot-spot region), or a specific site on DNA (such as the major groove). The natural function of the target could be stimulated (agonized), reduced (antagonized), unaffected, or completely changed by the binding of the reaction product. This will depend on the precise binding mode and the particular binding site the reaction product occupies on the target.

Functional sites (such as protein-protein interaction or catalytic sites) an proteins often are more prone to bind molecules than are other more neutral surface areas on a protein. In addition, these functional sites normally contain a smaller region that seems to be primarily responsible for the binding energy: the so-called "hot-spot regions" (Wells, et al. (1993) RECENT PROG. HORMONE RES. 48: 253-262). This phenomenon facilitates selection for molecules affecting the biological function of a certain target.

The linkage between the template molecule and reaction product allows rapid identification of binding molecules using various selection strategies. This invention broadly permits identifying binding molecules for any known target molecule. In addition, novel unknown targets can be discovered by isolating binding molecules against unknown antigens (epitopes) and using these binding molecules for identification and validation. In another preferred embodiment, the target molecule is designed to mimic a transition state of a chemical reaction; one or more reaction products resulting from the selection may stabilize the transition state and catalyze the chemical reaction.

(iii) Binding Assays

The template-directed synthesis of the invention permits selection procedures analogous to other display methods such as phage display (Smith (1985) SCIENCE 228: 1315-1317). Phage display selection has been used successfully on peptides (Wells et al. (1992) CURR. OP. STRUCT. BIOL. 2: 597-604), proteins (Marks et al. (1992) J. BIOL. CHEM. 267: 16007-16010) and antibodies (Winter et al. (1994) ANNU. REV. IMMUNOL. 12: 433-455). Similar selection procedures also are exploited for other types of display systems such as ribosome display Mattheakis et al. (1994) PROC. NATL. ACAD. SCI. 91: 9022-9026) and mRNA display (Roberts, et al. (1997) PROC. NATL. ACAD. SCI. 94:12297-302). The libraries of the present invention, however, allow direct selection of target-specific molecules without requiring traditional ribosome-mediated translation. The present invention also allows the display of small molecules which have not previously been synthesized directly from a nucleic acid template.

Selection of binding molecules from a library can be performed in any format to identify optimal binding molecules. Binding selections typically involve immobilizing the desired target molecule, adding a library of potential binders, and removing non-binders by washing. When the molecules showing low affinity for an immobilized target are washed away, the molecules with a stronger affinity generally remain attached to the target. The enriched population remaining bound to the target after stringent washing is preferably eluted with, for example, acid, chaotropic salts, heat, competitive elution with a known ligand or by proteolytic release of the target and/or of template molecules. The eluted templates are suitable for PCR, leading to many orders of amplification, whereby essentially each selected template becomes available at a greatly increased copy number for cloning, sequencing, and/or further enrichment or diversification.

In a binding assay, when the concentration of ligand is much less than that of the target (as it would be during the selection of a DNA-templated library), the fraction of ligand bound to target is determined by the effective concentration of the target protein. The fraction of ligand bound to target is a sigmoidal function of the concentration of target, with the midpoint (50% bound) at [target]=$K_d$ of the ligand-target complex. This relationship indicates that the stringency of a specific selection—the minimum ligand affinity required to remain bound to the target during the selection—is determined by the target concentration. Therefore, selection stringency is controllable by varying the effective concentration of target.

The target molecule (peptide, protein, DNA or other antigen) can be immobilized on a solid support, for example, a container wall, a wall of a microtiter plate well. The library preferably is dissolved in aqueous binding buffer in one pot and equilibrated in the presence of immobilized target molecule. Non-binders are washed away with buffer. Those molecules that may be binding to the target molecule through their attached DNA templates rather than through their synthetic moieties can be eliminated by washing the bound library with unfunctionalized templates lacking PCR primer binding sites. Remaining bound library members then can be eluted, for example, by denaturation.

Alternatively, the target molecule can be immobilized on beads, particularly if there is doubt that the target molecule will adsorb sufficiently to a container wall, as may be the case for an unfolded target eluted from an SDS-PAGE gel. The derivatized beads can then be used to separate high-affinity library members from nonbinders by simply sedimenting the beads in a benchtop centrifuge. Alternatively, the beads can be used to make an affinity column. In such cases, the library is passed through the column one or more times to permit binding. The column then is washed to remove nonbinding library members. Magnetic beads are essentially a variant on the above; the target is attached to magnetic beads which are then used in the selection.

There are many reactive matrices available for immobilizing the target molecule, including matrices bearing —$NH_2$ groups or —SH groups. The target molecule can be immobilized by conjugation with NHS ester or maleimide groups covalently linked to Sepharose beads and the integrity of known properties of the target molecule can be verified. Activated beads are available with attachment sites for —$NH_2$ or —COOH groups (which can be used for coupling). Alternatively, the target molecule is blotted onto nitrocellulose or PVDF. When using a blotting strategy, the blot should be blocked (e.g., with BSA or similar protein) after immobilization of the target to prevent nonspecific binding of library members to the blot.

Library members that bind a target molecule can be released by denaturation, acid, or chaotropic salts. Alternatively, elution conditions can be more specific to reduce background or to select for a desired specificity. Elution can be accomplished using proteolysis to cleave a linker between the target molecule and the immobilizing surface or between the reaction product and the template. Also, elution can be accomplished by competition with a known competitive ligand for the target molecule. Alternatively, a PCR reaction can be performed directly in the presence of the washed target molecules at the end of the selection procedure. Thus, the binding molecules need not be elutable from the target to be selectable since only the template is needed for further amplification or cloning, not the reaction product itself. Indeed, some target molecules bind the most avid ligands so tightly that elution would be difficult.

To select for a molecule that binds a protein expressible on a cell surface, such as an ion channel or a transmembrane receptor, the cells themselves can be used as the selection agent. The library preferably is first exposed to cells not expressing the target molecule on their surfaces to remove library members that bind specifically or non specifically to other cell surface epitopes. Alternatively, cells lacking the target molecule are present in large excess in the selection process and separable (by fluorescence-activated cell sorting (FACS), for example) from cells bearing the target molecule. In either method, cells bearing the target molecule then are used to isolate library members bearing the target molecule (e.g., by sedimenting the cells or by FACS sorting). For example, a recombinant DNA encoding the target molecule can be introduced into a cell line; library members that bind the transformed cells but not the untransformed cells are enriched for target molecule binders. This approach is also called subtraction selection and has successfully been used for phage display on antibody libraries (Hoogenboom et al. (1998) IMMUNOTECH 4: 1-20).

A selection procedure can also involve selection for binding to cell surface receptors that are internalized so that the receptor together with the selected binding molecule passes into the cytoplasm, nucleus, or other cellular compartment, such as the Golgi or lysosomes. Depending on the dissociation rate constant for specific selected binding molecules, these molecules may localize primarily within the intracellular compartments. Internalized library members can be distinguished from molecules attached to the cell surface by washing the cells, preferably with a denaturant. More preferably, standard subcellular fractionation techniques are used to isolate the selected library members in a desired subcellular compartment.

An alternative selection protocol also includes a known, weak ligand affixed to each member of the library. The known ligand guides the selection by interacting with a defined part of the target molecule and focuses the selection on molecules that bind to the same region, providing a cooperative effect. This can be particularly useful for increasing the affinity of a ligand with a desired biological function but with too low a potency.

Other methods for selection or partitioning are also available for use with the present invention. These include, for example: immunoprecipitation (direct or indirect) where the target molecule is captured together with library members; mobility shift assays in agarose or polyacrylamide gels, where the selected library members migrate with the target molecule in a gel; cesium chloride gradient centrifugation to isolate the target molecule with library members; mass spectroscopy to identify target molecules labeled with library members. In general, any method where the library member/target molecule complex can be separated from library members not bound to the target is useful.

The selection process is well suited for optimizations, where the selection steps are made in series, starting with the selection of binding molecules and ending with an optimized binding molecule. The procedures in each step can be automated using various robotic systems. Thus, the invention permits supplying a suitable library and target molecule to a fully automatic system which finally generates an optimized binding molecule. Under ideal conditions, this process should run without any requirement for external work outside the robotic system during the entire procedure.

The selection methods of the present invention can be combined with secondary selection or screening to identify reaction products capable of modifying target molecule function upon binding. Thus, the methods described herein can be employed to isolate or produce binding molecules that bind to and modify the function of any protein or nucleic acid. For example, nucleic acid-templated chemistry can be used to identify, isolate, or produce binding molecules (1) affecting catalytic activity of target enzymes by inhibiting catalysis or modifying substrate binding; (2) affecting the functionality of protein receptors, by inhibiting binding to receptors or by modifying the specificity of binding to receptors; (3) affecting the formation of protein multimers by disrupting the quaternary structure of protein subunits; or (4) modifying transport properties of a protein by disrupting transport of small molecules or ions.

Functional assays can be included in the selection process. For example, after selecting for binding activity, selected library members can be directly tested for a desired functional effect, such as an effect on cell signaling. This can, for example, be performed via FACS methodologies.

The binding molecules of the invention can be selected for other properties in addition to binding. For example, to select for stability of binding interactions in a desired working environment. If stability in the presence of a certain protease is desired, that protease can be part of the buffer medium used during selection. Similarly, the selection can be performed in serum or cell extracts or in any type of medium, aqueous or organic. Conditions that disrupt or degrade the template should however be avoided to allow subsequent amplification.

(iv) Other Selections

Selections for other desired properties, such as catalytic or other functional activities, can also be performed. Generally, the selection should be designed such that library members with the desired activity are isolatable on that basis from other library members. For example, library members can be screened for the ability to fold or otherwise significantly change conformation in the presence of a target molecule, such as a metal ion, or under particular pH or salinity conditions. The folded library members can be isolated by performing non-denaturing gel electrophoresis under the conditions of interest. The folded library members migrate to a different position in the gel and can subsequently be extracted from the gel and isolated.

Similarly, reaction products that fluoresce in the presence of specific ligands may be selected by FACS based sorting of translated polymers linked through their DNA templates to beads. Those beads that fluoresce in the presence, but not in the absence, of the target ligand are isolated and characterized. Useful beads with a homogenous population of nucleic acid-templates on any bead can be prepared using the split-pool synthesis technique on the bead, such that each bead is exposed to only a single nucleotide sequence. Alternatively, a different anti-template (each complementary to only a single, different template) can by synthesized on beads using a split-pool technique, and then can anneal to capture a solution-phase library.

Biotin-terminated biopolymers can be selected for the actual catalysis of bond-breaking reactions by passing these biopolymers over a resin linked through a substrate to avidin. Those biopolymers that catalyze substrate cleavage self-elute from a column charged with this resin. Similarly, biotin-terminated biopolymers can be selected for the catalysis of bond-forming reactions. One substrate is linked to resin and the second substrate is linked to avidin. Biopolymers that catalyze bond formation between the substrates are selected by their ability to react the substrates together, resulting in attachment of the biopolymer to the resin.

Library members can also be selected for their catalytic effects on synthesis of a polymer to which the template is or becomes attached. For example, the library member may influence the selection of monomer units to be polymerized as well as how the polymerization reaction takes place (e.g., stereochemistry, tacticity, activity). The synthesized polymers can be selected for specific properties, such as, molecular weight, density, hydrophobicity, tacticity, stereoselectivity, using standard techniques, such as, electrophoresis, gel filtration, centrifugal sedimentation, or partitioning into solvents of different hydrophobicities. The attached template that directed the synthesis of the polymer can then be identified.

Library members that catalyze virtually any reaction causing bond formation between two substrate molecules or resulting in bond breakage into two product molecules can be selected using the schemes proposed herein. To select for bond forming catalysts (for example, hetero Diels-Alder, Heck coupling, aldol reaction, or olefin metathesis catalysts), library members are covalently linked to one substrate through their 5' amino or thiol termini. The other substrate of the reaction is synthesized as a derivative linked to biotin. When dilute solutions of library-substrate conjugate are combined with the substrate-biotin conjugate, those library members that catalyze bond formation cause the biotin group to become covalently attached to themselves. Active bond forming catalysts can then be separated from inactive library members by capturing the former with immobilized streptavidin and washing away inactive library members In an analogous manner, library members that catalyze bond cleavage reactions such as retro-aldol reactions, amide hydrolysis, elimination reactions, or olefin dihydroxylation followed by periodate cleavage can be selected. In this case, library members are covalently linked to biotinylated substrates such that the bond breakage reaction causes the disconnection of the biotin moiety from the library members. Upon incubation under reaction conditions, active catalysts, but not inactive library members, induce the loss of their biotin groups. Streptavidin-linked beads can then be used to capture inactive polymers, while active catalysts are able to be eluted from the beads. Related bond formation and bond cleavage selections have been used successfully in catalytic RNA and DNA evolution (Jäschke et al. (2000) CURR. OPIN. CHEM. BIOL. 4: 257-62) Although these selections do not explicitly select for multiple turnover catalysis, RNAs and DNAs selected in this manner have in general proven to be multiple turnover catalysts when separated from their substrate moieties (Jäschke et al. (2000) CURR. OPIN. CHEM. BIOL. 4: 257-62; Jaeger et al. (1999) PROC. NATL. ACAD. SCI. USA 96: 14712-7; Bartel et al. (1993) SCIENCE 261: 1411-8; Sen et al. (1998) CURR. OPIN. CHEM. BIOL. 2: 680-7).

In addition to simply evolving active catalysts, the in vitro selections described above are used to evolve non-natural polymer libraries in powerful directions difficult to achieve using other catalyst discovery approaches. Substrate specificity among catalysts can be selected by selecting for active catalysts in the presence of the desired substrate and then selecting for inactive catalysts in the presence of one or more undesired substrates. If the desired and undesired substrates differ by their configuration at one or more stereocenters, enantioselective or diastereoselective catalysts can emerge from rounds of selection. Similarly, metal selectivity can be evolved by selecting for active catalysts in the presence of desired metals and selecting for inactive catalysts in the presence of undesired metals. Conversely, catalysts with broad substrate tolerance can be evolved by varying substrate structures between successive rounds of selection.

Importantly, in vitro selections can also select for specificity in addition to binding affinity. Library screening methods for binding specificity typically require duplicating the entire screen for each target or non-target of interest. In contrast, selections for specificity can be performed in a single experiment by selecting for target binding as well as for the inability to bind one or more non-targets. Thus, the library can be pre-depleted by removing library members that bind to a non-target. Alternatively, or in addition, selection for binding to the target molecule can be performed in the presence of an excess of one or more non-targets. To maximize specificity, the non-target can be a homologous molecule. If the target molecule is a protein, appropriate non-target proteins include, for example, a generally promiscuous protein such as an albumin. If the binding assay is designed to target only a specific portion of a target molecule, the non-target can be a variation on the molecule in which that portion has been changed or removed.

(vi) Amplification and Sequencing

Once all rounds of selection are complete, the templates which are, or formerly were, associated with the selected reaction product preferably are amplified using any suitable technique to facilitate sequencing or other subsequent manipulation of the templates. Natural oligonucleotides can be amplified by any state of the art method. These methods include, for example, polymerase chain reaction (PCR); nucleic acid sequence-based amplification (see, for example, Compton (1991) NATURE 350: 91-92), amplified anti-sense RNA (see, for example, van Gelder et al. (1988) PROC. NATL. ACAD. SCI. USA 85: 77652-77656); self-sustained sequence replication systems (Gnatelli et al. (1990) PROC. NATL. ACAD. SCI. USA 87: 1874-1878); polymerase-independent amplification (see, for example, Schmidt et al. (1997) NUCLEIC ACIDS RES. 25: 4797-4802, and in vivo amplification of plasmids carrying cloned DNA fragments. Descriptions of PCR methods are found, for example, in Saiki et al. (1985) SCIENCE 230: 1350-1354; Scharf et al. (1986) SCIENCE 233: 1076-1078; and in U.S. Pat. No. 4,683,202. Ligase-mediated amplification methods such as Ligase Chain Reaction (LCR) may also be used. In general, any means allowing faithful, efficient amplification of selected nucleic acid sequences can be employed in the method of the present invention. It is preferable, although not necessary, that the proportionate representations of the sequences after amplification reflect the relative proportions of sequences in the mixture before amplification.

For non-natural nucleotides the choices of efficient amplification procedures are fewer. As non-natural nucleotides can be incorporated by certain enzymes including polymerases it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al. (1997) NUCLEIC ACIDS RES. 25: 4797-4802). For backbone-modified oligonucleotides such as PNA and LNA, this amplification method may be used. Alternatively, standard PCR can be used to amplify a DNA from a PNA or LNA oligonucleotide template. Before or during amplification the templates or complementing templates may be mutagenized or recombined in order to create an evolved library for the next round of selection or screening.

(vii) Sequence Determination and Template Evolution

Sequencing can be done by a standard dideoxy chain termination method, or by chemical sequencing, for example, using the Maxam-Gilbert sequencing procedure. Alternatively, the sequence of the template (or, if a long template is used, the variable portion(s) thereof) can be determined by hybridization to a chip. For example, a single-stranded template molecule associated with a detectable moiety such as a fluorescent moiety is exposed to a chip bearing a large number of clonal populations of single-stranded nucleic acids or nucleic acid analogs of known sequence, each clonal population being present at a particular addressable location on the chip. The template sequences are permitted to anneal to the chip sequences. The position of the detectable moieties on the chip then is determined. Based upon the location of the detectable moiety and the immobilized sequence at that location, the sequence of the template can be determined. It is contemplated that large numbers of such oligonucleotides can be immobilized in an array on a chip or other solid support.

Libraries can be evolved by introducing mutations at the DNA level, for example, using error-prone PCR (Cadwell et al. (1992) PCR METHODS APPL. 2: 28) or by subjecting the DNA to in vitro homologous recombination (Stemmer (1994) PROC. NATL. ACAD. SCI. USA 91: 10747; Stemmer (1994) NATURE 370: 389) or by cassette mutagenesis.

(a) Error-Prone PCR

Random point mutagenesis is performed by conducting the PCR amplification step under error-prone PCR (Cadwell et al. (1992) PCR METHODS APPLIC. 2: 28-33) conditions. Because the genetic code of these molecules are written to assign related codons to related chemical groups, similar to the way that the natural protein genetic code is constructed, random point mutations in the templates encoding selected molecules will diversify progeny towards chemically related analogs. Because error-prone PCR is inherently less efficient than normal PCR, error-prone PCR diversification is preferably conducted with only natural dATP, dTTP, dCTP, and dGTP and using primers that lack chemical handles or biotin groups.

(b) Recombination

Libraries may be diversified using recombination. For example, templates to be recombined may have a structure in which codons are separated by five-base non-palindromic restriction endonuclease cleavage sites such as those cleaved by AvaII (G/GWCC, W=A or T), Sau96I (G/GNCC, N=A, G, T, or C), DdeI (C/TNAG), or HinFI (G/ANTC). Following selections, templates encoding desired molecules are enzymatically digested with these commercially available restriction enzymes. The digested fragments then are recombined into intact templates with T4 DNA ligase. Because the restriction sites separating codons are nonpalindromic, template fragments can only reassemble to form intact recombined templates. DNA-templated translation of recombined templates provides recombined small molecules. In this way, functional groups between synthetic small molecules with desired activities are recombined in a manner analogous to the recombination of amino acid residues between proteins in Nature. It is well appreciated that recombination explores the sequence space of a molecule much more efficiently than point mutagenesis alone (Minshull et al. (1999) CURR. OPIN. CHEM. BIOL. 3: 284-90; Bogarad et al. (1999) PROC. NATL. ACAD. SCI. USA 96: 2591-5; Stemmer NATURE 370: 389-391).

A preferred method of diversifying library members is through nonhomologous random recombination, as described, for example, in WO 02/074978; US Patent Application Publication No. 2003-0027180-A1; and Bittker et al. (2002) NATURE BIOTECH. 20(10): 1024-9.

(c) Random Cassette Mutagenesis

Random cassette mutagenesis is useful to create a diversified library from a fixed starting sequence. Thus, such a method can be used, for example, after a library has been subjected to selection and one or more library members have been isolated and sequenced. Generally, a library of oligonucleotides with variations on the starting sequence is generated by traditional chemical synthesis, error-prone PCR, or other methods. For example, a library of oligonucleotides can be generated in which, for each nucleotide position in a codon, the nucleotide has a 90% probability of being identical to the starting sequence at that position, and a 10% probability of being different. The oligonucleotides can be complete templates when synthesized, or can be fragments that are subsequently ligated with other oligonucleotides to form a diverse library of templates.

The following examples contain important additional information, exemplification and guidance that can be adapted to the practice of this invention in its various embodiments and equivalents thereof. Practice of the invention will be more fully understood from these following examples, which are presented herein for illustrative purpose only, and should not be construed as limiting in anyway.

EXAMPLES

Example 1

Small Molecule Diversity Accessed Through Iterated Branching Reaction Pathways Enabled by DNA-Templated Synthesis Nucleic acid mediated synthesis permits multiple, otherwise "incompatible" reaction types to occur in a single reaction vessel (Calderone et al. (2002), ANGEW. CHEM. 114: 4278; Calderone et al. (2002) AGNEW. CHEM INT. ED. 41: 4104) and also permits sequence-programmed subsets of reaction intermediates to be directed to specific reagents. These properties were integrated in this Example to perform DNA-templated synthesis of a highly diverse collection of molecules using iterated branching reaction pathways, in which intermediates undergo different types of reactions in each of two distinct steps. These findings demonstrate the promise of using iterated branching reaction pathways programmed by DNA sequences to allow access to small molecule diversity that would be difficult to create using standard solid-phase, split-pool synthesis.

To implement the concept of iterated branching reaction pathways in a DNA-templated format, a single solution containing five DNA templates was transformed into five diverse types of product structures, each arising from a unique sequence of reactions. A synthetic route was designed (FIG. 2) that combined previously developed base-labile sulfone (Gartner et al. (2002) J. AM. CHEM. SOC. 124: 10304) and thioester (Li et al. (2004) J. AM. CHEM. SOC. 126: 5090) linkers together with amine acylation (Gartner et al. (2002) ANGEW. CHEM., INT. ED. 41: 1796), aldehyde thiazolidination, Wittig olefination (Gartner et al. (2002) ANGEW. CHEM., INT. ED. 41: 1796), carboxylate amidation, and palladium-catalyzed cross-coupling chemistries (Gartner et al. (2002) ANGEW. CHEM., INT. ED. 41: 1796; Kanan et al. (2004) NATURE 431: 545).

In previous DNA-templated libraries (Gartner et al. (2004) SCIENCE 305: 1601), split-pool oligonucleotide synthesis was utilized to generate starting template pools in which every combination of reagent annealing templates ("codons") was represented. In the case of libraries constructed from branching reaction pathways, however, only a fraction of such a collection of templates would encode productive reaction sequences. For example, only 36% of the possible templates of the format [reaction 1 codon]-[reaction 2 codon]-[reaction 3 codon] encode three-step products in the branching library synthesis shown in FIG. 2. To address this problem, a cassette ligation strategy was developed to obtain starting template pools. In this strategy, single-stranded DNA overhangs at the ends of each cassette were designed such that ligation was only possible between adjacent cassettes that encode productive reaction sequences (see, Materials and Methods).

To validate each three-step pathway, the five syntheses were optimized individually such that all step 1 reactions, all step 2 reactions, and all step 3 reactions used reaction conditions a "b", or "c", respectively (FIGS. 3A-3C). Each pathway was individually executed starting with amine-terminated oligonucleotide 1. After each step, the reaction mixture was captured on immobilized streptavidin and washed with deionized water to remove any starting material template. Desired template-linked product eluted from the beads upon base-induced linker cleavage (Gartner et al. (2002) J. AM. CHEM. SOC. 124: 10304).

Figure 2:
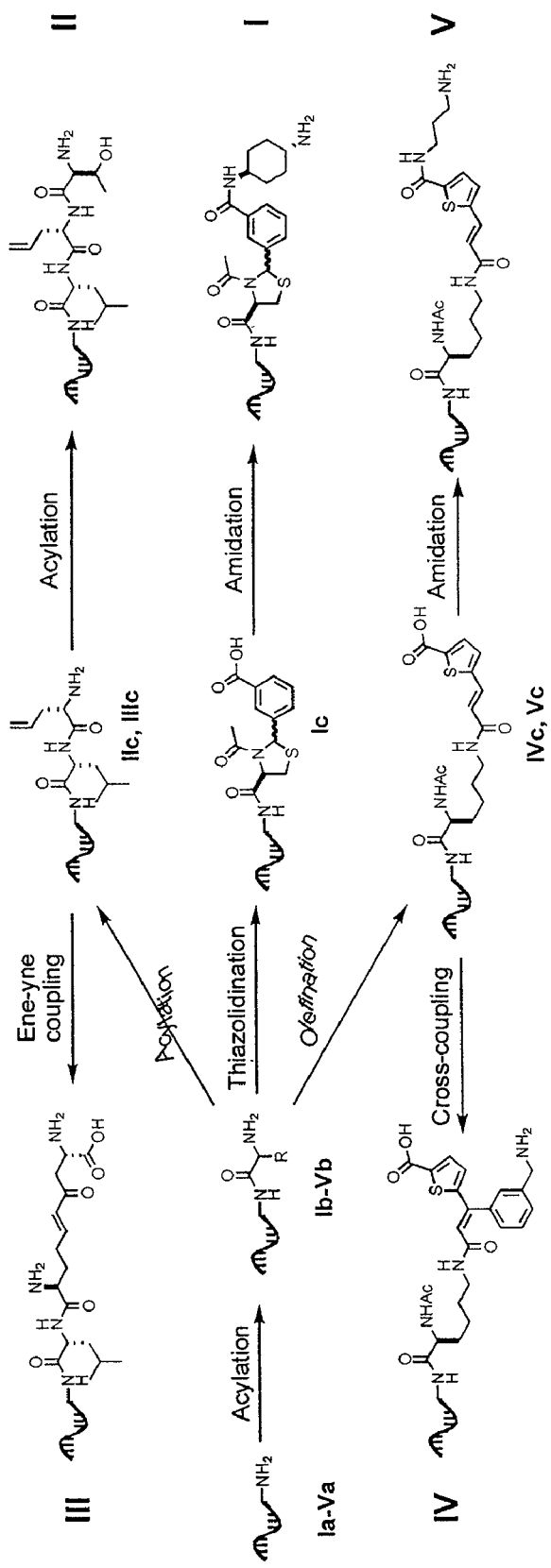
FIG. 2 is a schematic representation of a multi-step pathway for producing multiple compounds wherein multiple different compounds are simultaneously produced in each step by different chemical pathways.
Figure 4:
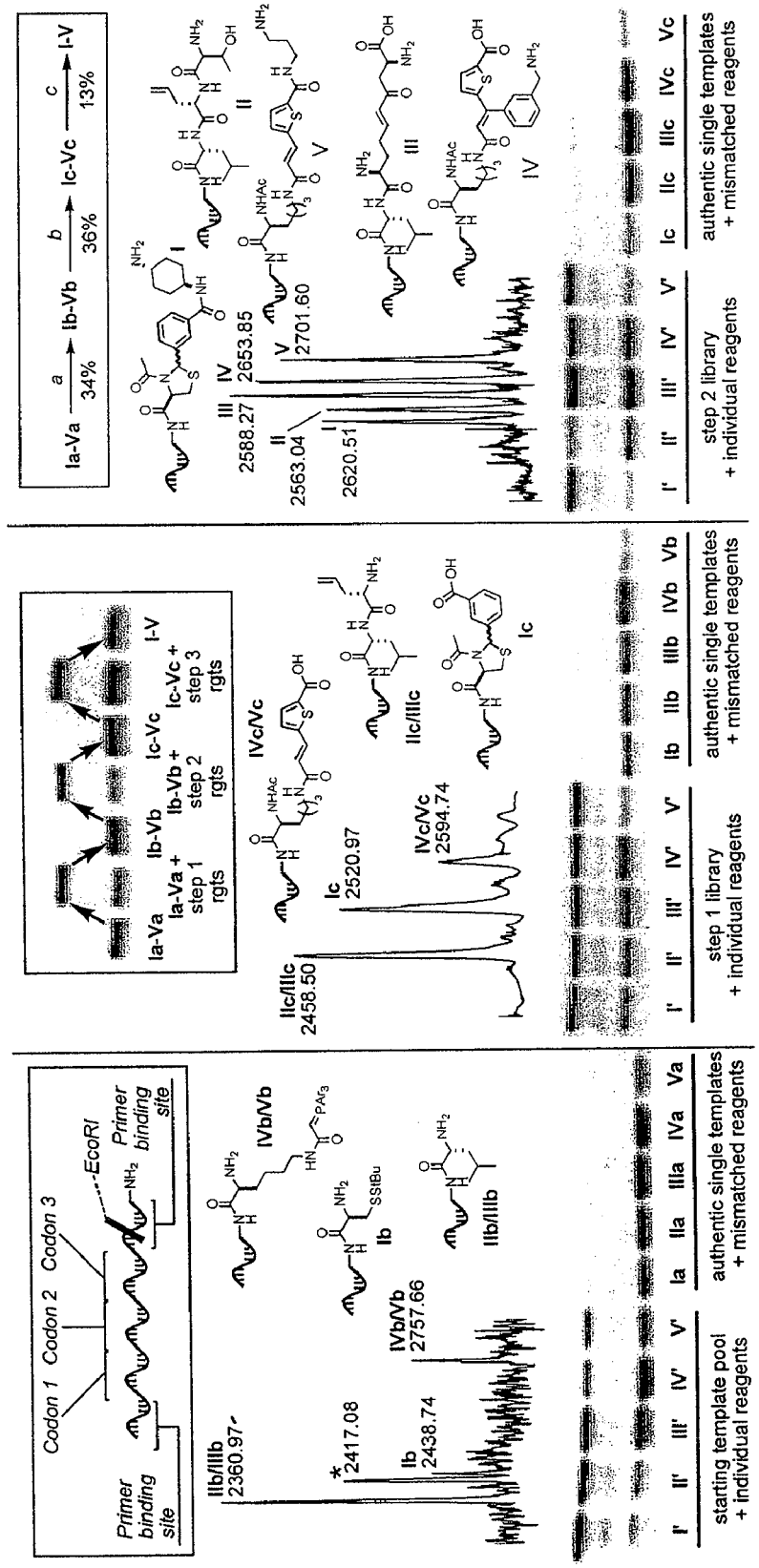
FIG. 4 shows the characterization of the three steps of the single reaction mixture (pooled) synthesis of compounds I-V via pathways I-V (see FIGS. 1 and 2). PAGE analysis of the three pooled steps is shown in the upper gel image. In the mass spectra of step 1, the peak denoted with an asterisk is a decomposition product arising from IVb and Vb during mass analysis. In each of the lower gels, the five lanes furthest on the left show the reaction of the starting template pool, the step 1 product pool, or the step 2 product pool with each of the reagents I'-V', which are reactive with and uniquely complementary to templates Ia-Va, respectively. The five lanes furthest on the right of each lower gel image show the reaction of individual starting materials for each step under conditions identical to those of actual library synthesis (see FIGS. 3A-3C), but with sequence mismatched reagents.

The reagents used in the experiments showing individual chemical pathways (FIG. 3) are denoted as 1-6, 8-13, and 16-21. However, the reagents used in the experiments with the combined pathways (FIG. 2 and FIG. 4) are denoted as Ia-Va, Ib-Vb, and Ic-Vc. The product of pathway I is denoted as 7 (FIG. 3) or I (FIG. 2 and FIG. 4), the product of pathway II is denoted as 14 (FIG. 3) or II (FIG. 2 and FIG. 4), the product of pathway III is denoted as 15 (FIG. 3) or III (FIG. 2 and FIG. 4), the product of pathway IV is denoted as 23 (FIG. 3) or IV (FIG. 2 and FIG. 4), and the product of pathway V is denoted as 22 (FIG. 3) or V (FIG. 2 and FIG. 4).

All five pathways (I-V) began with amine acylation (step 1). In step two—the first branching step—the step 1 products participated in one of three reactions (acylation, thiazolidine formation, or Wittig olefination) dictated by the identity of the previous reaction partner of each molecule. For example, the step 1 products containing phosphorane groups exclusively participated in step 2 Wittig olefination reactions. Step three represented a second branch point, in which each reaction type was dictated by the structure established in step 2.

Pathway I (FIG. 3A and FIG. 2) consists of amine acylation followed by thiazolidine formation and amidation. Disulfide-protected (L)-cysteine was sequence-specifically delivered to the template (1) upon addition of 1-ethyl-3-(3-dimethylaminopropyl)carbodiimide (EDC) and N-hydroxysulfosuccinimide (s-NHS) in 26% yield of isolated product. After disulfide reduction, treatment with a complementary DNA-linked thiol bearing 3-formylbenzoic acid for 90 minutes before addition of EDC/sNHS and acetylation yielded thiazolidine 5 in 44% yield. Treatment with Pd(II) at 37° C. for 4 hours and addition of EDC/s-NHS yielded product 7 in 15% yield (2% overall isolated yield over three steps, FIG. 3A).

Pathways II and III (FIG. 3B and FIG. 2) use identical reaction conditions as pathway I but effect two consecutive amine acylations in steps 1 and 2. The third step of pathway II consisted of a final amine acylation to yield a tripeptide, while the third step of pathway III uses a palladium catalyzed alkene-alkyne coupling reaction to generate an enone (Kanan et al. (2004) NATURE 431: 545). To validate these pathways, (D)-leucine and (L)-allylglycine were sequentially added to template 1 (steps 1 and 2) in 64% and 65% of the isolated products, respectively, to form 11. In step 3, the allylglycine was either acylated with (L)-threonine to yield tripeptide 14 in 20% yield (pathway III, 8.3% yield of the isolated product over three steps) or was cross-coupled (Kanan et al. (2004) supra) with the alkyne group in (L)-propargylglycine to yield enone 15 in 8% yield (pathway IV, 3.6% yield of the isolated product over three steps) (FIG. 3B).

Finally, pathways IV and V (FIG. 3C and FIG. 2) consisted of initial amine acylation followed by Wittig olefination. The third step of pathway IV was carboxylate amidation, while the third step in pathway V was a palladium-catalyzed Heck reaction. Thus, a lysine derivative bearing a side-chain phosphorane (16) was coupled to 1 (step 1) in 57% isolated yield followed by incubation with the DNA thioester of formylthiophene carboxylic acid (step 2) to yield 19 in 18% isolated yield. In the third step, treatment with amine 20 yielded disubstituted olefin 22 in 11% isolated yield (1.7% yield over three steps), while Heck coupling with aryl iodide 21 yielded trisubstituted olefin 23 in 10% isolated yield (0.8% yield over three steps, FIG. 3C).

All five pathways were monitored by gel electrophoresis and MALDI-TOF mass-spectrometric analysis. Each pathway yielded intermediates and final products whose electrophoretic behavior and mass spectra were consistent with the desired structures. The reaction sequences resulted in product yields similar to those reported for previous three-step DNA-templated synthetic sequences, despite requiring compromises among the different optimal reaction conditions in steps 2 and 3 (Gartner et al. (2002) J. AM. CHEM. SOC. 124: 10304; Gartner et al. (2004) SCIENCE 305: 1601; Li et al. (2004) J. AM. CHEM. SOC. 126: 5090).

Having verified each of the pathways individually, the simultaneous synthesis of I-V was performed in a single solution (FIG. 4). The ligated and gel-purified pool of templates was treated with 1.5 equivalents of each functionalized reagent DNA per step and was incubated under the same conditions used to verify each pathway individually. After each step, only the presence of desired products was observed by nuclease digestion followed by MALDI-TOF mass spectrometry. To evaluate the sequence specificity of each reaction, each step was repeated using reagents linked to non-complementary (mismatched) oligonucleotides. No significant product formation (<5%) was observed (FIG. 4). Because not all five templates yield step 1 and step 2 products that are distinguishable by mass, an aliquot of material at each step was treated with a reactive oligonucleotide uniquely complementary to each template (I'-V'), converting a portion of each pool into a higher molecular weight species and confirming that all five templates were present at every step (see, Materials and Methods).

Starting from 8 nmol of template, 125 pmol of I-V were obtained corresponding to an average overall isolated yield of 1.6%. This quantity of material even if hypothetically divided among thousands of library members is sufficient for >1000 in vitro selections and PCR-based amplifications needed to identify library members with desired properties (Gartner et al. (2004) SCIENCE 305: 1601). The initial use of iterated branching reaction pathways demonstrates the promise of such an approach in the synthesis of diverse libraries, for example, small-molecule libraries that would be challenging to create using current library synthesis methods. The structures created in this work also include several of the most complex synthetic small-molecule products translated from DNA to date.

Materials and Methods

The reagents for producing products 7, 14, 15, 22, and 23 separately (FIGS. 3A-3C) or products I, II, III, IV, and V via a single reaction mixture (i.e., pooled synthesis) (FIG. 2 and FIG. 4) were prepared by similar schemes, as described below.

(1) Abbreviations

The following abbreviations are used below: BSOCOES (bis[2-(succinimidyloxycarbonyloxy)-ethyl]sulfone); CAPS (3-(cyclohexylamino)-1-propanesulfonic acid); CPG (controlled pore glass); DMF (dimethylformamide); DTT (dithiothreitol); EDC (1-ethyl-3-(3-dimethylaminopropyl)carbodiimide); EPPS (N-(2-hydroxyethyl)piperazine-N'-3-propanesulfonic acid); MES (2-morpholinoethanesulfonic acid); MOPS (3-morpholinopropanesulfonic acid); s-NHS (N-hydroxysulfosuccinimide); and TEAA (triethylammonium acetate).

(2) General Experimental Methods

DNA oligonucleotides were synthesized using standard phosphoramidite coupling methods using an Applied Biosystems Expedite oligonucleotide synthesizer. All CPG, reagents, and phosphoramidites were obtained from Glen Research (Sterling, Va.). 5'-aminooligonucleotides were synthesized using 5'-Amino-Modifier 5,5'-biotinylated oligonucleotides were synthesized using 5'-Biotin Phosphoramidite, 3'-biotinylated oligonucleotides were synthesized using Biotin TEG CPG, 3'-aminooligonucleotides were synthesized using 3'-Amino-Modifier C7 CPG, 3'-thiooligonucleotides were synthesized using 3'-Thiol-Modifier C3 S-S CPG, and 5'-phosphooligonucleotides were synthesized using Chemical Phosphorylation Reagent II. After synthesis, oligonucleotides were cleaved from the solid phase and deprotected by treatment with 1:1 concentrated ammonia: 40% aqueous methylamine for 10 minutes at 65° C. Where necessary, monomethoxytrityl and dimethoxytrityl groups were removed by treatment with 4% aqueous trifluoroacetic acid for 5 minutes at 23° C. before quenching with an equal volume of 2 M TEAA, pH 7.0. 5'-phosphates were liberated after detritylation by treatment with 2:1 water:concentrated ammonia for 15 minutes at 23° C. Oligonucleotides were purified by reverse phase HPLC on a C18 stationary phase using a 0.1 M TEAA pH 7.0/acetonitrile gradient and appropriate fractions were lyophilized. Oligonucleotides were quantitated by UV/vis spectrophotometry or densitometry of ethidium bromide-stained gels. Unless otherwise noted, all other chemicals were obtained from Sigma-Aldrich (Milwaukee, Wis.).

(3) DNA Labeling

Reagents 2, 6, 8, 10, 12, 13, 16, 20, 21, Ia'-Va', IIb', IIIb', and Ic'-Vc'. 3.3 µL of a 300 mM aqueous solution of the appropriate small molecule amine (in the case of amino acids, 300 mM NaOH was added to aid solubility) was added to the appropriate 3'-aminooligonucleotide in 86.7 µL of 200 mM sodium phosphate buffer, pH 7.2. 10 µL of 100 mM BSOCOES (Pierce, Rockford, Ill.) in DMF was then added and reactions were agitated for 2 hours, desalted by gel filtration (NAP-5 columns, Amersham Biosciences, Uppsala, Sweden) and purified by reverse phase HPLC. In the case of 16, IVa' and Va', the small molecule amine was (2S)-(+)-2-amino-6-iodoacetamidohexanoic acid (Alexis, San Diego, Calif.), and prior to desalting, 20 µL of 20 mg/mL sodium diphenylphosphinobenzene-3-sulfonate (TCI America, Portland, Oreg.) in water was added and the reaction mixture was incubated for an additional 2 hours before purification. In the case of 20 and Vc', the oligonucleotide was coupled with Fmoc-diaminopropane hydrochloride (Novabiochem, San Diego, Calif.). Deprotection of the amine was achieved by addition of 2 µL of triethylamine prior to lyophilization.

Reagents 4, 18, Ib', IVb', and Vb'. The appropriate small molecule acid, EDC, and s-NHS were combined at 150 mM each in 9:1 DMF:water and incubated at 23° C. for 2 h. Meanwhile, the appropriate 3'-thiooligonucleotide was dissolved in 90 µL 25 mM DTT, 100 mM EPPS pH 8.5 and incubated for 1 hour to reduce the disulfide. The reduced thiooligonucleotide was buffer-exchanged into 200 mM sodium phosphate pH 7.2 using Centri-Sep columns (Princeton Separations, Adelphia, N.J.) and 10 µl of the acid/EDC/s-NHS mixture was added. The reaction was incubated for 2 hours at 23° C., desalted using NAP-5 columns, and purified by reverse phase HPLC.

3'-carboxylate reagents I'-V'. I'-V' were dissolved in 90 µL 200 mM sodium phosphate. 10 µL of 20 mg/mL succinic anhydride were added, and the reaction mixture was incubated for 1 hour at 23° C. and buffer exchanged into deionized water using Centri-Sep columns. The desalted labeled oligonucleotide was used without purification.

The identities of all oligonucleotide reagents were confirmed by MALDI-TOF mass spectrometry.

(4) Template Assembly

Templates were assembled from three oligonucleotide cassettes: (i) the 3' cassette containing a primer-binding site necessary for selections and the first reaction codon; (ii) the internal cassette containing the second reaction codon; and (iii) the 5' cassette containing a reactive primary amine group, a primer-binding sequence including an EcoRI cleavage site, and the third reaction codon. Oligonucleotides were combined in 50 mM Tris-HCl, 10 mM $MgCl_2$, mM DTT, 1 mM ATP, 25 µg/mL bovine serum albumin (T4 DNA ligase buffer, New England Biolabs, Beverly, Mass.) to form each cassette individually at a final concentration of 12 µM. Cassettes were then combined in the relative ratio I:II:III:IV:V 0.75:0.75:1.75:3.5:3.25, and 1/50 volume of T4 DNA ligase (New England Biolabs) was added. The ratio of cassettes was empirically determined to yield a similar amount of each structure in the final product pool. Ligation mixtures were incubated at 16° C. for 12 h before PAGE purification. DNA was excised from the gel, isolated by the crush and soak method and ethanol precipitated.

(5) DNA-Templated Chemistry

FIGS. 3A-3C (individual synthesis reactions) or FIGS. 2 and 4 (single reaction mixture synthesis) conditions a. Templates 1 (see FIG. 3) or I-V (see FIGS. 2 and 4) were present at 60 nM total; reagents 2, 8, 16 (see FIG. 3), or Ia'-Va' (see FIGS. 2 and 4) were present at 90 nM total. Reactions were performed in 100 mM MES buffer, 1 M NaCl, 20 mM EDC, 15 mM s-NHS, pH 6.0. Reactions were incubated 12 hours at 23° C. A small aliquot was withdrawn for gel analysis, and the reaction mixture was added to 1.05 equivalents of streptavidin-linked magnetic particles (Roche, Indianapolis, Ind.) prewashed with 5 mL of 10 mM Tris-HCl, 1 mM EDTA, 100 mM NaCl pH 7.5. The reaction mixture was incubated with the magnetic particles 30 min at 23° C., and the supernatant removed. Beads were washed three times with a reaction volume of deionized water; gel analysis showed that in general, all unreacted template was removed in the first two washes. After washing, product purity was verified by withdrawing a small aliquot of magnetic particles and heating in 1 mM biotin, 10 mM Tris-HCl, 1 mM EDTA pH 7.5 15 minutes at 85° C. to elute captured DNA from the beads. The remainder of the magnetic particles was treated with 100 mM CAPS pH 10.0 for 2 hours at 37° C. to cleave the linker and liberate product templates. Products 3, 9, 17 (see FIG. 3), or Ia-Va (see FIGS. 2 and 4) were isolated by ethanol precipitation.

FIGS. 3A-3C (individual synthesis reactions) or FIGS. 2 and 4 (single reaction mixture synthesis) conditions b. Templates 3, 9, 17 (see FIG. 3), or Ia-Va (see FIGS. 2 and 4) were treated in 1 mL 25 mM DTT, 100 mM EPPS pH 8.5 for 1 hour at 37° C. and then desalted by gel filtration (NAP-10 columns, Amersham). Reduced, desalted templates were diluted to a total concentration of 78 nM with 250 mM MOPS, 1.25 M NaCl, pH 7.0 and 117 nM total of reagents 4, 10, 18 (see FIG. 3), or Ib'-Vb' (see FIGS. 2 and 4). After 90 min at 23° C., 200 mM EDC and 150 mM s-NHS were added to a final concentration of 20 mM EDC and 15 mM s-NHS, and the reaction was incubated for 12 hours at 23° C. 1/200 volume of acetic anhydride was added and the reaction mixture was further incubated 1 hour at 23° C. Product isolation was accomplished as above, with the exception that cleavage was effected by treatment with 100 mM CAPS 10 mM 2-mercaptoethanol pH 12.0 for 1 hour at 37° C.

FIGS. 3A-3C (individual synthesis reactions) or FIGS. 2 and 4 (single reaction mixture synthesis) conditions c. Templates 5, 11, 19 (see FIG. 3), or Ib-Vb (see FIGS. 2 and 4) were dissolved at a total concentration of 60 nM in a solution containing 100 mM MES, 1 M NaBr, pH 6.0, and 90 nM total reagents 6, 12, 13, 20, 21 (see FIG. 3), or Ic'-Vc' (see FIGS. 2 and 4). 1/100 volume of 50 mM $Na_2PdC4$ preincubated in 100 mM MES, 1 M NaBr, pH 6.0 for 20 minutes was added, and the reaction mixture was incubated at 37° C. for 4 hour. 1 M DTT was added to 20 mM final concentration, and the reaction mixture was heated to 85° C. for 15 minutes and buffer exchanged (NAP-10) into fresh 125 mM MES, 1.25 M NaBr pH 6.0; reaction volume was adjusted to a total template and reagent concentration of 40 nM and 60 nM, respectively. 200 mM EDC and 150 mM s-NHS were added to final concentrations of 20 mM and 15 mM, respectively, and the reaction mixture was incubated at 23° C. for 12 hours. Product isolation was accomplished as above, with the exception that cleavage was effected by treatment with 100 mM CAPS pH 12.0 for 30 minutes at 23° C.

(6) Library Analysis

Mismatch control. Authentic samples of I-V, Ia-Va, and Ib-Vb (see FIG. 4) were individually generated either by automated oligonucleotide synthesis in the cases of I-V or by DNA-templated synthesis in the cases of Ia-Va and Ib-Vb. Each was individually treated under conditions identical to those used in the actual library synthesis, but with its complementary reagent oligonucleotide omitted, ethanol precipitated, and analyzed by PAGE.

Template verification. Aliquots of library intermediate pools were withdrawn prior to each step and treated separately with complementary reagents I'-V' (see FIG. 3). I'-V' were labeled at their 3'-termini with either amines or carboxylates and the appropriately labeled reagent was selected for each pool to ensure reactivity: For I-V and Ia-Va, 3'-carboxylate I'-V' were used; for Ib-Vb, 3'-carboxylate II' and III' and 3'-amino I', IV', and V' were used. In each case, 10 pmol of template pool was combined in 160 µL 100 mM MES, 1 M NaCl, 20 mM EDC, 15 mM s-NHS pH 6.0 with 5 pmol of the appropriate reagent and incubated 12 h at 23° C. Reactions were then ethanol precipitated and analyzed by PAGE.

(7) MALDI Analysis

Product aliquots were combined with 1.5 equivalents of 3',5'-bisbiotinylated oligonucleotides to reconstitute a double-stranded EcoRI recognition site in 100 mM Tris-HCl, 50 mM NaCl, 10 mM $MgCl_2$, 0.025% Triton X-100 pH 7.5 (EcoRI buffer, New England Biolabs). Digestion mixtures were heated to 85° C. briefly and allowed to cool slowly to 23° C. 1/50 volume of EcoRI (New England Biolabs) was added, and digests were incubated at 37° C. for 12 h. Digests were added to 1.05 equivalents of streptavidin-linked magnetic particles prewashed with 200 µL of 10 mM Tris-HCl, 1 mM EDTA, 100 mM NaCl pH 7.5 and incubated for 30 min at 23° C. The supernatant was removed, and the magnetic particles were washed with 50 µL of deionized water. The wash and supernatant were combined and ethanol precipitated. The isolated DNA was then resuspended in 20 µL of 0.1 M TEAA pH 7.0, desalted by ZipTip (Millipore, Billerica, Mass.), and spotted in a 9:1 40 mg/mL trishydroxyacetophenone/50 mg/mL ammonium citrate matrix in 50% aqueous acetonitrile.

Mass spectra of oligonucleotides containing phosphoranes (17, IVa'/Va', IVb/Vb) gave a side product of mass consistent with loss of the phoshane group, but it was not fully characterized. This side product arose during the MALDI-TOF mass analysis and was otherwise not present based on the following experiment. Phosphorane-containing DNA, previously observed to contain the spurious species by mass spectrometry but consisting of a single species by HPLC, was treated in 200 mM sodium phosphate pH 8.0 with 2 mg/mL 4-formylbenzoic acid (2 hours, 37° C.). By HPLC, the conversion was >95% to a single species. The reaction mixture was desalted and spotted onto the MALDI plate as above without purification, and only the expected cinnamide-containing oligonucleotide was observed in the mass spectrum with no evidence of the unknown side product, suggesting that material maintained Wittig olefination reactivity despite the apparent presence of a species lacking the phosphorane in the mass spectrum.

(8) DNA Sequences

DNA sequences used in this work are shown below. Sequences corresponding to the first, second, and third reaction codons are shown as boxed, double-underlined, and dashed-underlined, respectively. EcoRI sites are single-underlined, and ligation sites for the template assembly are denoted in bold italics in the template and cassette sequences. The template used in the individual reaction pathways is denoted as 1. The templates used for combined reaction pathways are denoted as I-V.

Template Sequences:

```
1:    5'H2N-CCATGCGAAT TCCATACCAGTC AGCACACTGTAG CACGTTCTGAGCCTGC    (SEQ ID NO. 1)

I:    5'H2N-CCATGCGAAT TCTAGGTAGTAC TGTGCGATTGTG TCCCTAAAGCTTCCTCAC  (SEQ ID NO. 2)

II:   5'H2N-CCATGCGAAT TCATACGGTAAC ACTGCCTTTCTC CCATCAAAGCTTCCTCAC  (SEQ ID NO. 3)

III:  5'H2N-CCATGCGAAT TCTATCCGATTG ACTGCCTTTCTC CCATCAAAGCTTCCTCAC  (SEQ ID NO. 4)

IV:   5'H2N-CCATGCGAAT TCTTCTTCCTTC AGCCTAGTAGTC CGTAGAAAGCTTCCTCAC  (SEQ ID NO. 5)

V:    5'H2N-CCATGCGAAT TCAACAACGTAG AGCCTAGTAGTC CGTAGAAAGCTTCCTCAC  (SEQ ID NO. 6)
```

Reagent sequences: The oligonucleotides used in the reagents for the individual pathway reactions are denoted 2, 4, 6, 8, 10, 12, 13, 16, 18, 20, and 21. The oligonucleotides used in the reagents for the combined reaction pathways are denoted as Ia'-Vc'. Mismatched bases are in lower case.

```
2, 8, 16:
3'H2N-GGTACTCGTGCAAGA-biotin        (SEQ ID NO. 7)

4, 10, 18:
3'H2N/HS-GGTACTCGTGTGAGCA-biotin    (SEQ ID NO. 8)

6, 12, 13, 20, 21:
3'H2N-GGTAC AGGTATGGTCAG -biotin    (SEQ ID NO. 9)

mis, steps 1 and 2:
3'H2N/HS-GGTACTCcTGCAtGA            (SEQ ID NO. 10)

mis, step 3:
3'H2N-GGTACAGGaAaGcaCAG             (SEQ ID NO. 11)

Ia':
3'H2N-GGTAAACAGGGATTT-biotin        (SEQ ID NO. 12)

IIa'/IIIa':
3'H2N-GGTAAAGGGTAGTTT-biotin        (SEQ ID NO. 13)

IVa'/Va':
3'H2N-GGTAAAGGCATCTTT-biotin        (SEQ ID NO. 14)

Ib':
3'HS-GGTACAACACGCTAAC-biotin        (SEQ ID NO. 15)

IIb'/IIIb':
3'H2N-GGTACATGACGGAAAG-biotin       (SEQ ID NO. 16)

IVb'/Vb':
3'HS-GGTACATCGGATCATC-biotin        (SEQ ID NO. 17)

Ic':
3'H2N-GGTAC AGATCCATCATG -biotin    (SEQ ID NO. 18)

IIc':
3'H2N-GGTAC AGTATGCCATTG -biotin    (SEQ ID NO. 19)

IIIc':
3'H2N-GGTAC AGATAGGCTAAC -biotin    (SEQ ID NO. 20)

IVc':
3'H2N-GGTAC AGAACAAGGAAG -biotin    (SEQ ID NO. 21)

Vc':
3'H2N-GGTAC AGTTGTTGCATC -biotin    (SEQ ID NO. 22)
```

Cassette sequences: "P" denotes a 5'-phosphate; sequences denoted by asterisks are ligated in the antisense strand.

```
I.3:    5'H2N-CCATGCGAAT TCTAGGTAGT     (SEQ ID NO. 23)
I.3*:   3'- ATCCATCATG AC -P            (SEQ ID NO. 24)
I.2:    5'P- AC TG TGCGAT               (SEQ ID NO. 25)
I.2*:   3'-ACGCTAACAC-P                 (SEQ ID NO. 26)
I.1:    5'P-TGTGTCCCTAAAGCTTCCTCAC      (SEQ ID NO. 27)
I.1*:   3'-AGGGATTT                     (SEQ ID NO. 28)
II.3:   5'H2N-CCATGCGAAT TCATACGGTA     (SEQ ID NO. 29)
II.3*:  3'- TATGCCATTG TG -P            (SEQ ID NO. 30)
II.2:   5'P- AC ACTGCCTT                (SEQ ID NO. 31)
II.2*:  3'-ACGGAAAGAG-P                 (SEQ ID NO. 32)
II.1:   5'P-TCTCCCATCAAAGCTTCCTCAC      (SEQ ID NO. 33)
II.1*:  3'-GGTAGTTT                     (SEQ ID NO. 34)
III.3:  5'H2N-CCATGCGAAT TCTATCCGAT     (SEQ ID NO. 35)
III.3*: 3'- ATAGGCTAAC TG                (SEQ ID NO. 36)
III.2:  5'P- TG ACTGCCTT                (SEQ ID NO. 37)
III.2*: 3'-ACGGAAAGAG-P                 (SEQ ID NO. 38)
III.1:  5'P-TCTCCCATCAAAGCTTCCTCAC      (SEQ ID NO. 39)
III.1*: 3'-GGTAGTTT                     (SEQ ID NO. 40)
IV.3:   5'-H2N-CCATGCGAAT TCTTGTTCCT    (SEQ ID NO. 41)
IV.3*:  3'- AACAAGGAAG TC -P            (SEQ ID NO. 42)
IV.2:   5'P- TC AGCCTAGT                (SEQ ID NO. 43)
IV.2*:  3'-GGATCGTCAG-P                 (SEQ ID NO. 44)
IV.1:   5'P-AGTCCGTAGAAAGCTTCCTCAC      (SEQ ID NO. 45)
IV.1*:  3'-GCATCTTT                     (SEQ ID NO. 46)
V.3:    5'H2N-CCATGCGAAT TCAACAACGT     (SEQ ID NO. 47)
V.3*:   3'- TTGTTGCATC TC               (SEQ ID NO. 48)
V.2:    5'P- AG AGCCTAGT                (SEQ ID NO. 49)
V.2*:   3'-GGATCATCAG-P                 (SEQ ID NO. 50)
V.1:    5'P-AGTCCGTAGAAAGCTTCCTCAC      (SEQ ID NO. 51)
V.1*:   3'-GCATCTTT                     (SEQ ID NO. 52)
```

EcoRI complement for 1: 3'biotin-GGTACG CTTAAGGTAGTGG-biotin (SEQ ID NO. 53)
EcoRI complement for I-V: 3'biotin-GGTACG CTTAAG-biotin (SEQ ID NO. 54)

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A multi-step in vitro method for producing multiple reaction products in a single reaction mixture, the method comprising the steps of:
    (a) combining in a reaction vessel
        (i) a plurality of different templates, wherein each template comprises a reactive unit associated with an oligonucleotide sequence comprising a plurality of codons wherein at least two templates comprise at least one different codon and the reactive units associated with the at least two templates have the same chemical functionality, and
        (ii) a plurality of different transfer units, wherein each transfer unit comprises a reactive unit associated with an oligonucleotide sequence comprising an anti-codon capable of annealing to a codon present in at least one of the templates
        under conditions to permit a plurality of transfer units to anneal to a corresponding plurality of templates so that the reactive units of each template react with the reactive unit of each transfer unit to produce a plurality of reaction intermediates, wherein each reaction intermediate is associated with the template that encoded its synthesis; and
    (b) combining in the same reaction vessel or in a different reaction vessel
        (i) the plurality of reaction intermediates, and
        (ii) a plurality of transfer units, wherein each transfer unit comprises a reactive unit associated with an oligonucleotide sequence comprising an anti-codon capable of annealing to a codon present in at least one of the templates,
        under conditions to permit a plurality of the transfer units to anneal to a corresponding plurality of templates so that the reactive unit of each transfer unit reacts with at least one reaction intermediate to produce a plurality of reaction products, wherein each reaction product is associated with the template that encoded its synthesis;
    wherein at least two of the reaction intermediates in step (a) are produced by different chemical reactions.

2. The method of claim 1, comprising the additional step of, after step (b), selecting a reaction product associated with a template oligonucleotide that encoded its synthesis.

3. The method of claim 1, wherein at least three of the reaction intermediates are produced by different chemical reactions.

4. The method of claim 1, wherein, in step (b), at least two of the reaction products are produced by different chemical reactions.

5. The method of claim 4, wherein at least three of the reaction products are produced by different chemical reactions.

6. A multi-step in vitro method for producing multiple reaction products in a single reaction mixture, the method comprising the steps of:
    (a) combining in a single solution
        (i) a first template comprising a first reactive unit associated with an oligonucleotide sequence comprising a first codon and a second codon,
        (ii) a second template comprising the first reactive unit of the first template associated with an oligonucleotide sequence comprising a first codon and a second codon, wherein the first codons of the first and second templates have the same oligonucleotide sequences, and wherein the second codons of the first and second templates have different oligonucleotide sequences,
        (iii) a third template comprising a second reactive unit associated with an oligonucleotide sequence comprising a first codon and a second codon, wherein the first and second codons of the third template have different oligonucleotide sequences from the first and second codons of both the first and second templates, and wherein the second reactive unit is different from the first reactive unit,
        (iv) at least two first transfer units each comprising the same first reactive unit associated with an oligonucleotide sequence comprising an anti-codon capable of annealing to a codon sequence present in both the first and second templates, and
        (v) a second transfer unit comprising a second reactive unit associated with an oligonucleotide sequence comprising an anti-codon capable of annealing to a codon sequence present in the third template, wherein the second reactive unit is different from the first transfer unit and the second transfer unit does not anneal to a codon sequence present in the first or second templates,
        under conditions to permit
        (i) a first transfer unit to anneal to the first template so that the first reactive unit of the template reacts with the first reactive unit of the transfer unit to produce a first reaction intermediate associated with the first template,
        (ii) another first transfer unit to anneal to the second template so that the first reactive unit of the second template reacts with the first reactive unit of the transfer unit to produce a second reaction intermediate associated with the second template, and
        (iii) the second transfer unit to anneal to the third template so that the second reactive unit of the second transfer unit reacts with the second reactive unit of the third template to produce a third reaction intermediate associated with the third template; and
    (b) harvesting the first reaction intermediate, the second reaction intermediate, and third reaction intermediate; and
    (c) combining in a single solution
        (i) the first reaction intermediate, the second reaction intermediate, and third reaction intermediate,
        (ii) a third transfer unit comprising a third reactive unit associated with an oligonucleotide sequence comprising an anti-codon capable of annealing to a codon sequence present in the first template,
        (iii) a fourth transfer unit comprising a fourth reactive unit associated with an oligonucleotide sequence comprising an anti-codon capable of annealing to a codon sequence present in the second template, and
        (iv) a fifth transfer unit comprising a fifth reactive unit associated with an oligonucleotide sequence comprising an anti-codon capable of annealing to a codon sequence present in the third template,
        under conditions to permit
        (i) the third transfer unit to anneal to the first template so that the third reactive unit of the third transfer unit reacts with the first reaction intermediate to produce a first product,
        (ii) the fourth transfer unit to anneal to the second template so that the fourth reactive unit of the fourth transfer unit reacts with the second reaction intermediate to produce a second product, and
        (iii) the fifth transfer unit to anneal to the third template so that the fifth reactive unit of the fifth transfer unit reacts with the third reaction intermediate to produce a third product.

7. The method of claim 6, comprising the additional step of, after step (c), selecting a reaction product associated with a template oligonucleotide that encoded its synthesis.

8. The method of claim 7, wherein, in step (a), the second and third reaction intermediates are produced by different chemical reactions.

9. The method of claim 7, wherein, in step (a), the first, second, and third reaction intermediates are produced by different chemical reactions.

10. The method of claim 7, wherein, in step (c), the second and third reaction products are produced by different chemical reactions.

11. The method of claim 7, wherein, in step (c), the first, second, and third reaction products are produced by different chemical reactions.

12. A multi-step in vitro method for producing multiple reaction products in a single reaction mixture, the method comprising the steps of:
   (a) combining in a single solution
      (i) a first template comprising a first reactive unit associated with an oligonucleotide sequence comprising first codon and a second codon,
      (ii) a second template comprising the first reactive unit of the first template associated with an oligonucleotide sequence comprising a first codon and a second codon, wherein the first codons of the first and second templates have the same oligonucleotide sequences, and wherein the second codons of the first and second templates have different oligonucleotide sequences,
      (iii) a third template comprising a second reactive unit associated with an oligonucleotide sequence comprising first codon and a second codon, wherein the first and second codons of the third template have different oligonucleotide sequences from the first and second codons of both the first and second templates, and wherein the second reactive unit is different from the first reactive unit,
      (iv) a first transfer unit each comprising a first reactive unit associated with an oligonucleotide sequence comprising an anti-codon capable of annealing to a codon sequence present in the first template,
      (v) a second transfer unit each comprising a second reactive unit associated with an oligonucleotide sequence comprising an anti-codon capable of annealing to a codon sequence present in the second template, wherein the second reactive unit associated with the second transfer unit is different from the first reactive unit associated with the first transfer unit; and the second transfer unit does not anneal to a codon sequence present in the first template, and
      (vi) a third transfer unit comprising a third reactive unit associated with an oligonucleotide sequence comprising an anti-codon capable of annealing to a codon sequence present in the third template, wherein the third reactive unit is different from the first or second reactive units; and the third transfer unit does not anneal to a codon sequence present in the first or second template,
   under conditions to permit
      (i) the first transfer unit to anneal to the first template so that the first reactive unit of the first template reacts with the first reactive unit of the transfer unit to produce a first reaction intermediate associated with the first template,
      (ii) the second transfer unit to anneal to the second template so that the second reactive unit of the second template reacts with the second reactive unit of the transfer unit to produce a second reaction intermediate associated with the second template, and
      (iii) the third transfer unit to anneal to the third template so that the third reactive unit of the third transfer unit reacts with the third reactive unit of the third template to produce a third reaction intermediate associated with the third template; and
   (b) harvesting the first reaction intermediate, the second reaction intermediate, and third reaction intermediate; and
   (c) combining in a single solution
      (i) the first reaction intermediate, the second reaction intermediate, and third reaction intermediate,
      (ii) a fourth transfer unit comprising a fourth reactive unit associated with an oligonucleotide sequence comprising an anti-codon capable of annealing to a codon sequence present in the first template, and
      (iv) a fifth transfer unit comprising a fifth reactive unit associated with an oligonucleotide sequence comprising an anti-codon capable of annealing to a codon sequence present in the third template,
   under conditions to permit
      (i) the fourth transfer unit to anneal to the first template so that the fourth reactive unit of the fourth transfer unit reacts with the first reaction intermediate to produce a first product, and
      (ii) the fifth transfer unit to anneal to the third template so that the fifth reactive unit of the fifth transfer unit reacts with the third reaction intermediate to produce a third product.

13. The method of claim 12, wherein the single solution in step (c) further comprises a sixth transfer unit comprising a sixth reactive unit associated with an oligonucleotide sequence comprising an anti-codon capable of annealing to a codon sequence present in the second template and the sixth transfer unit anneals to the second template so that the sixth reactive unit of the sixth transfer unit reacts with the second reaction intermediate to produce a second product.

14. The method of claim 12, comprising the additional step of, after step (c), selecting a reaction product associated with a template oligonucleotide that encoded its synthesis.

15. The method of claim 12, wherein, in step (a), the first and second reaction intermediates are produced by different chemical reactions.

16. The method of claim 12, wherein, in step (a), the first, second and third reaction intermediates are produced by different chemical reactions.

17. The method of claim 12, wherein, in step (c), the first and second reaction products are produced by different chemical reactions.

18. The method of claim 12, wherein, in step (c), the first, second and third reaction products are produced by different chemical reactions.

* * * * *

UNITED STATES PATENT AND TRADEMARK OFFICE
CERTIFICATE OF CORRECTION

PATENT NO. : 8,183,178 B2
APPLICATION NO. : 11/917609
DATED : May 22, 2012
INVENTOR(S) : Christopher T. Calderone et al.

It is certified that error appears in the above-identified patent and that said Letters Patent is hereby corrected as shown below:

In the Specification

At Column 1, Lines 17-21, please change the paragraph:
"This invention was made with Government support under the Office of Naval Research awards N00014-03-1-0749, N00014-00-1-0596, and National Institutes of Health award GM65865. The Government has certain rights in the invention."

To:
-- This invention was made with government support under N00014-00-1-0596 and N00014-03-1-0749 awarded by U.S. Office of Naval Research (NAVY/ONR) and under GM065865 awarded by National Institutes of Health (NIH). The government has certain rights in the invention. --

Signed and Sealed this
Ninth Day of September, 2025

Coke Morgan Stewart
*Acting Director of the United States Patent and Trademark Office*